United States Patent
Ke et al.

(10) Patent No.: US 7,255,984 B2
(45) Date of Patent: *Aug. 14, 2007

(54) COMBINATION THERAPY FOR OSTEOPOROSIS

(75) Inventors: Hua Zhu Ke, Ledyard; David D. Thompson, Gales Ferry, both of CT (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/736,051

(22) Filed: Dec. 13, 2000

(65) Prior Publication Data

US 2001/0009920 A1 Jul. 26, 2001

Related U.S. Application Data

(62) Division of application No. 09/117,972, filed as application No. PCT/IB96/01462 on Dec. 23, 1996, now Pat. No. 6,323,232.
(60) Provisional application No. 60/012,412, filed on Feb. 28, 1996.

(51) Int. Cl.
 *C12Q 1/00* (2006.01)
 *G01N 33/53* (2006.01)

(52) U.S. Cl. .................. 435/4; 435/520; 435/975; 514/428

(58) Field of Classification Search .......... 435/4, 435/975, 520; 424/520; 514/428

See application file for complete search history.

(56) References Cited

U.S. PATENT DOCUMENTS

| | | | |
|---|---|---|---|
| 4,097,601 A | 6/1978 | Schaaf | 424/269 |
| 4,621,100 A | 11/1986 | Lund et al. | 514/573 |
| 4,894,373 A | 1/1990 | Young | 514/239.2 |
| 5,118,667 A | 6/1992 | Adams et al. | 514/12 |
| 5,164,368 A | 11/1992 | Recker et al. | 514/12 |
| 5,216,183 A | 6/1993 | Sugiura et al. | 549/546 |
| 5,281,590 A | 1/1994 | Husa et al. | 514/211 |
| 5,409,911 A | 4/1995 | Tyler et al. | 514/91 |
| 5,441,966 A | 8/1995 | Dodge | 514/324 |
| 5,492,916 A | 2/1996 | Morriello et al. | 514/318 |
| 5,510,370 A | 4/1996 | Hock | 514/443 |
| 5,767,124 A | 6/1998 | Draper et al. | 514/278 |
| 5,773,477 A | 6/1998 | McLean et al. | 514/648 |
| 6,043,026 A | 3/2000 | Patchett et al. | 435/4 |
| 6,100,301 A | 8/2000 | McLean et al. | 514/648 |
| 6,110,918 A | 8/2000 | Busch et al. | 514/255 |
| 6,110,932 A * | 8/2000 | Carpino et al. | 514/303 |
| 6,132,774 A * | 10/2000 | Ke et al. | 424/520 |
| 6,245,765 B1 | 6/2001 | Busch et al. | 514/252.13 |
| 6,323,232 B1 | 11/2001 | Ke et al. | 514/408 |

FOREIGN PATENT DOCUMENTS

| | | |
|---|---|---|
| CA | 2128376 | 7/1994 |
| EP | 0 381 296 | 2/1990 |
| EP | 0514720 | 5/1992 |
| EP | 0509317 | 10/1993 |
| EP | 0605193 | 12/1993 |
| EP | 0 635 270 | 1/1995 |
| EP | 0635270 | 1/1995 |
| EP | 0904774 | 9/1998 |
| PE | 246921.94 | 2/1994 |
| WO | WO 95/11029 | * 4/1995 |
| WO | WO 95/14666 | 6/1995 |
| WO | WO 9621656 | 7/1996 |
| WO | WO 9724369 | 7/1997 |
| WO | WO 9731640 | 9/1997 |
| WO | WO 97/46252 | 12/1997 |

OTHER PUBLICATIONS

ASBMR 18th Annual Meeting, XP: 000652812, (1996).
Cheng et al., Bone, vol. 17, No. 4 (suppl.) pp. 329s–334s 1995.
Kudo et al., Journal of Endocrinology, vol. 150, pp. 223–229, 1996.
Fournier et al., Journal of Endocrinilogy, vol. 150, pp. 275–285, 1996.
Ke et al., Bone and Mineral, vol. 19, pp. 45–62, 1992.
Adachi, Journal of Rheumatology, vol. 23 Supp 45, pp. 11–14, (1996).
Kimmel et al., Osteoporosis, vol. 20, No. 3, pp. 735–758, 1994.
E. Seeman, et al., Bone, vol. 17, No. 2 Suppl. pp. 23s–29s, (1996).
D. Thompson et al., Journal of Bone and Mineral Research, vol. 11, p. S95, Aug., 1996.
Pienta, et al., The Prostate, 23, pp. 61–67, 1993.
Neubauer et al., The Prostate, 23, pp. 245–262, 1993.
Martindale, The Estra Pharmacopia, The Parm. Press, London, pp. 477 and 500, 1993.
Cheng et al., *Journal of Shanghai Medical*, "Combined use of tamoxifen and DL–15–methyl prostaglandin F2 for termination of early pregnacy", vol. 17, pp. 378–381 (1990) XP008065947 (Abstract in English only).
Williams et al, American Society of Consultant Pharmacists, pp. 1–26, "New Drugs for 1996".*
Bachmann, G.A. Nonhormonal Alternatives for the Management of Early Menopause in Younger Women with Breast Cancer; Journal of the Nat. Cancer Inst., Monographs, (1994) (16) pp. 161–167.*

(Continued)

*Primary Examiner*—Patricia Leith
(74) *Attorney, Agent, or Firm*—Gregg C. Benson; John A. Wichtowski

(57) ABSTRACT

Pharmaceutical combination compositions including certain estrogen agonists/antagonists and prostaglandins or prostaglandin agonists/antagonists. The compositions are useful for the treatment of bone disorders including osteoporosis.

41 Claims, No Drawings

OTHER PUBLICATIONS

Wronski et al., Endocrinology, V. 132(2), pp. 823-831, (1993).*
Patchett et al, Proc. Natl. Academy of Science, USA, vol. 92, pp. 7001-7005, (Jul. 1995).*
Lax et al, Endocrinology, V.113(5), p. 1043-1055, (1983).*
Evans et al., Endocrinology, V.134(5), pp. 2282-2288, May 1994, Abstract Only.*
Lax et al., Antagonistic Action of Eatrogens, Flutamide, and Human Growth Human Growth Hormone on Androgen-Induced Changes in the Activities of Some Enzymes of Hepatic Steroid Metabolism In the Rat. Endocrinology 113(3):1043-1055 (1983).
Wronski et al., Parathyroid Hormone is More Effective tha Estrogen or Bisphosphonates for Restoration of Lost Bone Mass in Ovarieotomized Rats. Endocrinology 132(2):823-831 (1993).
Evans et al., The Effects of Raloxifene on Tibia Histomorphometry in Ovariectomized Rats. Endocrinology 134(5):2283-2288 (1994).

Budavari et al., eds. The Merck Index, 12th Edition, entry for #8864 Somatotropin. Whitehouse Station, NJ: Merck Research Laboratories, 1996, pp. 1488-1489.
Ke, et al., *Endocrinology*, "Droloxifene, a new estrogen antagonist/agonist, prevents bone loss in ovariectomized rats" vol. 136. pp. 2435-2441, (1995).
Meng, et al., *Journal of Bone and Mineral Research*, "Temporal Expression of the Anabolic Action of PTH in Cancellous Bone of Ovariectomized Rats", vol. 11, pp. 421-429, (1996).
Neubauer et al., *Prostat*, Endocrine and antiprostatic effects of raloxifene (LY156758) in the male rat,.vol. 23(3), pp. 245-62, (1993).
*The Merck Index*, $11^{th}$ Edition, pp. 1113, 1114, 1251, (1989).
*The Merck Index*, $12^{th}$ Edition, pp. 582, 1394, 1548, (1996).
Bachmann, Gloria A, *Journal of National Cancer Institute Monographs*, Nongormonal Alternatives for the Management of Early Menopause in Younger Women with Breast Cancer, vol. 16, pp. 161-167, (1994).

* cited by examiner

COMBINATION THERAPY FOR OSTEOPOROSIS

CROSS-REFERENCE TO RELATED APPLICATIONS

This is a division of U.S. Ser. No. 09/117,972, filed Aug. 11, 1998 now U.S. Pat. No. 6,323,232, entitled "Combination Therapy for Osteoperosis", which is a 371 of application Ser. No. PCT/IB96/09462, filed Dec. 23, 1996, which claims priority to U.S. Provisional Application Number 60/012,412 filed Feb. 28, 1996.

BACKGROUND OF THE INVENTION

This invention relates to a pharmaceutical combination of estrogen agonists/antagonists and agents that stimulate bone formation and increase bone mass, kits containing such combinations and the use of such combinations to treat conditions which present with low bone mass in mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase threefold over the next 60 years, and one study estimates that there will be 4.5 million hip fractures worldwide in 2050.

Women are at greater risk of osteoporosis than men. Women experience a sharp acceleration of bone loss immediately following menopause. Other factors that increase bone loss leading to osteoporosis include smoking, alcohol abuse, a sedentary lifestyle and low calcium intake.

Estrogen is the agent of choice in preventing osteoporosis or post menopausal bone loss in women. In addition, Black, et al. in EP 0605193A1 report that estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer, endometrial cancer and possibly breast cancer, causing many women to either avoid this treatment or take the medication for only a short period of time. Although the risk of endometrial cancer is thought to be reduced by a concurrent use of a progesterone, there is still concern about possible increased risk of breast cancer with the use of estrogen. Recently suggested therapeutic regimens, which seek to lessen the cancer risk, such as administering combinations of progesterone and estrogen, cause the patient to experience unacceptable bleeding. Furthermore, combining progesterone with estrogen seems to blunt the serum cholesterol lowering effects of estrogen. The significant undesirable side effects associated with estrogen therapy support the need to develop alternative therapies for osteoporosis that have the desirable beneficial effect on serum LDL but do not cause undesirable side effects.

Recently, a number of estrogen agonists/antagonists have been proposed for treatment of osteoporosis. It has been reported (Osteoporosis Conference Scrip No. 1812/13 Apr. 16/20, 1993, p. 29) that raloxifene, 6hydroxy-2-(4-hydroxyphenyl)-3-[4-(2-piperidinoethoxy)benzoyl]benzo[b]thiophene, mimics the favorable action of estrogen on bone and lipids but, unlike estrogen, has minimal uterine stimulatory effect. [Black, L. J. et al., Raloxifene (LY139481 Hcl) Prevents Bone Loss and Reduces Serum Cholesterol Without Causing Uterine Hypertrophy in Ovariectomized Rats, J. Clin. Invest., 1994, 93:63–69].

Also, tamoxifen, 1-(4-β-dimethylaminoethoxyphenyl)-1,2-diphenyl-but-1-ene, is an antiestrogen that is proposed as an osteoporosis agent which has a palliative effect on breast cancer, but is reported to have some estrogenic activity in the uterus. Gill-Sharma, et al., *J. Reproduction and Fertility* (1993) 99, 395, disclose that tamoxifen at 200 and 400 mg/kg/day reduces the weights of the testes and secondary sex organs in male rats.

In addition U.S. Pat. No. 5,254,594 (the disclosure of which is hereby incorporated by reference) discloses the use of droloxifene for the treatment of bone diseases including osteoporosis.

Agents such as droloxifene prevent bone loss and thereby reduce the risk of fracture without estrogen's side effects. However, estrogen and estrogen agonists alone are only expected to reduce the fracture risk by about 50% leaving approximately 50% of ostepenic women still at risk for an osteoporotic fracture.

Nonestogen agonists/antagonists such as bisphosphonates are also proposed for the treatment of osteoporosis. For example, Fosamax® is a bisphosphonate that is currently marketed for the treatment of osteoporosis. Other bisphosphonates currently undergoing regulatory review include risedronate, tiludronate, and ibandronate.

Frost et al. in "Treatment of Osteoporosis by Manipulation of Coherent Bone Cell Populations", *Clinical Orthopedics and Related Research*, 143, 227 (1979) discloses a theoretical model that suggests it should be possible to synchronize the activity and metabolism of bone cells by administering a bone cell activating agent first, followed by a bone resorption inhibiting agent and then normal bone formation is allowed to occur.

Tang et al., *Restoring and Maintaining Bone in Osteogenic Female Rat Skeleton: I. Changes in Bone Mass and Structure*, J. Bone Mineral Research 7 (9), p1093–1104, 1992 discloses data for the lose, restore and maintain (LRM) concept, a practical approach for reversing existing osteoporosis. The LRM concept uses anabolic agents to restore bone mass and architecture (+ phase) and then switches to an agent with the established ability to maintain bone mass, to keep the new bone (+/− phase). The rat study utilized $PGE_2$ and risedronate, a bisphosphonate, to show that most of the new cancellous and cortical bone induced by $PGE_2$ can be maintained for at least 60 days after discontinuing $PGE_2$ by administering risedronate.

Combinations of bisphosphonates and prostaglandins for the treatment of osteoporosis are disclosed. E.P. App. No. 0 381 296 teaches the use of a kit wherein a bone activating period or treatment regime is followed by a bone resorption inhibiting regime. Examples of bone activating compounds cited in this reference include parathyroid hormone (PTH), inorganic phosphate, growth hormone, fluoride, thyroid hormone (e.g., thyroxin), certain vitamin D metabolites and prostaglandins ($PGE_2$ in a dose regime of 10 mg/kg per day). Polyphosphonates are disclosed as the bone resorption inhibiting agents.

PCT/US93/08529 discloses the simultaneous delivery of a bone activating agent such as a prostaglandin that is chemically coupled to a bone resorption inhibiting compound which selectively delivers the bone activating agent to the target area. Upon gradual hydrolysis of the novel compound, the hydrolyzed products are able to provide bone resorption inhibiting activity (via the bisphosphonates) and bone growth or stimulating activity (via $PGE_2$).

The effects of a combination of prostaglandin E2 and risedronate (a bisphosphonate) was studied in Lin et al., *Effects of Prostaglandin E2 and Risedronate Administration on Cancellous Bone in Older Female Rats*, Bone 15 (5), p489–496, 1994.

Qiu et al., *Experimental Study on Antiatherosclerotic Treatment by $PGE_2$ Combined With Vitamin E and Estradiol*, Chinese Medical Journal, 108 (1) p33–36, 1995 disclose that a single dose of $PGE_2$ combined with vitamin E and with estradiol had more coordinative inhibition on aortic and coronary atherosclerotic lesions, as well as on platelet aggregation, smooth muscle cell proliferation and lipid peroxidation than that of a single dose of $PGE_2$.

The abstract for "Nonhormnonal Alternatives for the Management of Early Menopause in Younger Women with Breast Cancer", Monogr. Nat. Cancer Inst. (16), 161–167, 1994, states "The use of several nonestrogen approaches for the prevention and treatment of osteoporosis has been promising. Traditional recommendations to maintain skeletal integrity, such as weight-bearing exercise; a diet rich in calcium and limited in caffeine, alcohol, and protein; avoidance of smoking; and measures to minimize trauma have been expanded to include the use or investigation of drugs (either alone or in combination). These drugs include progestins, vitamin D metabolites, injectable and intranasal synthetic salmon calcitonin, bisphosphonates, sodium fluoride, parathyroid hormone, growth factors, tamoxifen, etc."

Thus, although there exist a variety of osteoporosis therapies there is a continuing need and a continuing search in this field of art for alternative therapies due to only limited success of current therapies in reducing osteoporotic fractures.

SUMMARY OF THE INVENTION

This invention is directed to a pharmaceutical composition including estrogen agonists/antagonists and anabolic agents and for the use of such compositions for the treatment of conditions which present with low bone mass, including osteoporosis in mammals (e.g., humans, particularly women).

The combination comprises a therapeutically effective amount of a first compound, said first compound being an estrogen agonlist/antagonist; and a therapeutically effective amount of a second compound, said second compound being a prostaglandin or a prostaglandin agonist/antagonist.

Preferred estrogen agonist/antagonists include droloxifene, raloxifene, tamoxifen, 4-hydroxy-tamoxifen,
Cis-6-(4-fluoro-phenyl)-5-[4-(2-piperidin-1-yl-ethoxy) phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene-2-ol;
Cis-1-[6'-pyrrolodinoethoxy-3'-pyridyl]-2-phenyl-6-hydroxy-1,2,3,4-tetrahydrohaphthalene;
1-(4'-Pyrroldinoethoxyphenyl)-2-(4'-fluorophenyl)-6-hydroxy-1,2,3,4-tetrahydroisoquinoline;
Cis-6-(4-hydroxyphenyl)-5-[4-(2-pipeidin-1-yl-ethoxy)-phenyl]-5,6,7,8-tetrahydronaphthalene-2-ol; and
1-(4'-Pyrrolidinolethoxyphenyl)-2-phenyl-6-hydroxy-1,2,3,4-tetrahydroisoquinoline.

Preferred anabolic agents include $PGD_1$, $PGD_2$, $PGE_2$, $PGE_1$, $PGF_2$, $PGF_2\alpha$ and 3S-(3-Hydroxyphenyl-4-phenyl-butyl)-2R-[6-(1H-tetrazol-5-yl)-hexyl]-cyclopentanone.

Another aspect of this invention is a method for treating mammals which present with low bone mass comprising administering to a mammal having a condition which presents with low bone mass
a. a therapeutically effective amount of a first compound, said first compound being an estrogen agonist/antagonist; and
b. a therapeutically effective amount of a second compound, said second compound being a prostaglandin or a prostaglandin agonist/antagonist.

Preferred estrogen agonist/antagonists in this method include droloxifene, raloxifene, tamoxifen, 4-hydroxy-tamoxifen,
Cis-6-(4-fluoro-phenyl)-5-[4-(2-piperidin-1-yl-ethoxy)-phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene-2-ol;
Cis-1-[6'-pyrrolodinoethoxy-3'-pyridyl]-2-phenyl-6-hydroxy-1,2,3,4-tetrahydrohaphthalene;
1-(4'-Pyrroldinoethoxyphenyl)-2-(4'-fluorophenyl)-6-hydroxy-1,2,3,4-tetrahydroisoquinoline;
Cis-6-(4-hydroxyphenyl)-5-[4-(2-piperidin-1-yl-ethoxy)-phenyl]-5,6,7,8-tetrahydronaphthalene2-ol; and
1-(4'-Pyrrolidinolethoxyphenyl)-2-phenyl-6-hydroxy-1,2,3,4-tetrahydroisoquinoline.

Preferred anabolic agents in this method include $PGD_1$, $PGD_2$, $PGE_2$, $PGE_1$, $PGF_2$, $PGF_2\alpha$ and 3S-(3-Hydroxy-4-phenyl-butyl)-2R-[6-(1H-tetrazol-5-yl)-hexyl]-cyclopentanone.

A preferred aspect of this method is wherein the condition which presents with low bone mass is osteoporosis.

Another preferred aspect of this method is wherein the first compound and the second compound are administered substantially simultaneously.

Another preferred aspect of this method is wherein the second compound is administered for a period of from about three months to about three years.

Optionally the administration of the second compound is followed by administration of the first compound for a period of from about three months to about three years without the administration of the second compound during the second period of from about three months to about three years.

Alternatively, the administration of the second compound is followed by administration of the first compound for a period greater than about three years without the administration of the second compound during the greater than about three year period.

Another aspect of this invention is a synergistic pharmaceutical composition comprising
a. an amount of a first compound, said first compound being an estrogen agonist/antagonist; and
b. an amount of a second compound, said second compound being a prostaglandin or a prostaglandin agonist/antagonist
wherein the amount of the first compound alone and the amount of the second compound alone is insufficient to achieve the therapeutic effects of increase in bone formation and decrease in bone resorption if administered simultaneously and wherein the combined effect of the amounts of the first and second compounds is greater than the sum of the therapeutic effects achievable with the individual amounts of the first and second compound, and a pharmaceutically acceptable diluent or carrier.

Yet another aspect of this invention is a synergistic method for treating mammals which present with low bone mass comprising administering to a mammal having a condition which presents with low bone mass
   a. an amount of a first compound, said first compound being an estrogen agonist/antagonist; and
   b. an amount of a second compound, said second compound being a prostaglandin or a prostaglandin agonist/antagonist wherein the amount of the first compound alone and the amount of the second compound alone is insufficient to achieve the therapeutic effects of increase in bone formation and decrease in bone resorption if administered simultaneously and wherein the combined effect of the amounts of the first and second compounds is greater than the sum of the therapeutic effects achievable with the individual amounts of the first and second compound, and a pharmaceutically acceptable diluent or carrier.

Another aspect of this invention is a kit containing a treatment for a condition which presents with low bone mass comprising:
   a. a therapeutically effective amount of an estrogen agonist/antagonist and a pharmaceutically acceptable carrier in a first unit dosage form;
   b. a therapeutically effective amount of a prostaglandin or a prostaglandin agonist/antagonist and a pharmaceutically acceptable carrier in a second unit dosage form; and
   c. container means for containing said first and second dosage forms.

Another aspect of this invention is directed to a pharmaceutical composition comprising:
   a. a therapeutically effective amount of a first compound, said first compound being droloxifene, raloxifene, tamoxifen or idoxifene; and
   b. a therapeutically effective amount of a second compound, said second compound being sodium fluoride or N-[1-(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677.

A preferred aspect of this composition is wherein the first compound is droloxifene.

Another aspect of this invention is directed to a method for treating mammals which present with low bone mass comprising administering to a mammal having a condition which presents with low bone mass
   a. a therapeutically effective amount of a first compound, said first compound being droloxifene, raloxifene, tamoxifen or idoxifene; and
   b. a therapeutically effective amount of a second compound, said second compound being sodium fluoride or N-[1-(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677.

A preferred aspect of this method is wherein the first compound is droloxifene.

Another preferred aspect of this method is wherein the condition which presents with low bone mass is osteoporosis.

Another preferred aspect of this method is wherein the first compound and the second compound are administered substantially simultaneously.

Another preferred aspect of this method is wherein the second compound is administered for a period of from about three months to about three years.

Optionally the administration of the second compound is followed by administration of the first compound for a period of from about three months to about three years without the administration of the second compound during the period of from about three months to about three years.

Alternatively, the administration of the second compound is followed by administration of the first compound for a period greater than about three years without the administration of the second compound during the greater than about three year period.

Another aspect of this invention is a synergistic pharmaceutical composition comprising
   a. an amount of a first compound, said first compound being droloxifene, raloxifene, tamoxifen or idoxifene; and
   b. an amount of a second compound, said second compound being sodium fluoride or N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677 wherein the amount of the first compound alone and the amount of the second compound alone is insufficient to achieve the therapeutic effects of increase in bone formation and decrease in bone resorption if administered simultaneously and wherein the combined effect of the amounts of the first and second compounds is greater than the sum of the therapeutic effects achievable with the individual amounts of the first and second compound, and a pharmaceutically acceptable diluent or carrier.

A preferred aspect of this synergistic composition is wherein the first compound is droloxifene.

Yet another aspect of this invention is a synergistic method for treating mammals which present with low bone mass comprising administering to a mammal having a condition which presents with low bone mass
   a. an amount of a first compound, said first compound being droloxifene, raloxifene, tamoxifen or idoxifene; and
   b. an amount of a second compound, said second compound being sodium fluoride or N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677 wherein the amount of the first compound alone and the amount of the second compound alone is insufficient to achieve the therapeutic effects of increase in bone formation and decrease in bone resorption if administered simultaneously and wherein the combined effect of the amounts of the first and second compounds is greater than the sum of the therapeutic effects achievable with the individual amounts of the first and second compound, and a pharmaceutically acceptable diluent or carrier.

A preferred aspect of this synergistic method is wherein the first compound is droloxifene.

Another aspect of this invention is a kit containing a treatment for a condition which presents with low bone mass comprising:
   a. a therapeutically effective amount of droloxifene, raloxifene, tamoxifen or idoxifene and a pharmaceutically acceptable carrier in a first unit dosage form;
   b. a therapeutically effective amount of sodium fluoride or N-[1- (R)-[1,2-Dihydro-1-methanesulfonylspiro[3H-indole-3,4'-piperidin]-1'-yl)carbonyl]-2-

(phenylmethyloxy)ethyl]-2amino-2-methylpropanamide:MK-677 and a pharmaceutically acceptable carrier in a second unit dosage form; and c. container means for containing said first and second dosage forms.

A preferred aspect of this kit is wherein the first compound is droloxifene.

Yet another aspect of this invention is a pharmaceutical composition comprising:

a. a therapeutically effective amount of a first compound, said first compound being
Cis-6-(4-fluoro-phenyl)-5-[4-(2-piperidin-1-yl-ethoxy)-phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene-2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;
Cis-6-(4-hydroxyphenyl)-[4-(2-piperidin-1-yl-ethoxyyphenyl]-5,6,7,8-tetrahydronaphthalene2-ol; or
1-(4'-Pyrrolidinolethoxyphenyl)-2-phenylthydroxy-1,2,3,4-tetrahydroisoquinoline; and b. a therapeutically effective amount of a second compound, said second compound being sodium fluoride, a parathyroid hormone, growth hormone or a growth hormone secretagogue.

Yet another aspect of this invention is a method for treating mammals which present with low bone mass comprising administering to a mammal having a condition which presents with low bone mass a. a therapeutically effective amount of a first compound, said first compound being
Cis-6-(4-fluoro-phenyl)-5-[4(2-piperidin-1-yl-ethoxy)-phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;
Cis-6-(4-hydroxyphenyl)-5-[4-(2-piperidin-1-yl-ethoxy)-phenyl]-5,6,7,8-tetrahydronaphthalene-2-ol; or
1-(4-Pyrrolidinolethoxyphenyl)-2-phenyl-6-hydroxy-1,2,3,4-tetrahydroisoquinoline; and b. a therapeutically effective amount of a second compound, said second compound being sodium fluoride, a parathyroid hormone, growth hormone or a growth hormone secretagogue.

A preferred aspect of this method is wherein the condition which presents with low bone mass is osteoporosis.

Another preferred aspect of this method is wherein the first compound and the second compound are administered substantially simultaneously.

Another preferred aspect of this method is wherein the second compound is administered for a period of from about three months to about three years.

Optionally the administration of the second compound is followed by administration of the first compound for a period of from about three months to about three years without the administration of the second compound during the period of from about three months to about three years.

Alternatively, the administration of the second compound is followed by administration of the first compound for a period greater than about three years without the administration of the second compound during the greater than about three year period.

Yet another aspect of this invention is a synergistic pharmaceutical composition comprising a. an amount of a first compound, said first compound being
Cis-6-(4-fluoro-phenyl)-5-[4-(2-piperidin-1-yl-ethoxy)-phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;
Cis-6-(hydroxyphenyl)-5-[4-(2-piperidin-1-yl-ethoxy)-phenyl]-5,6,7,8-tetrahydronaphthalene-2-ol; or
1-(4'-Pyrrolidinolethoxyphenyl)-2-phenylthydroxy-1,2,3,4-tetrahydroisoquinoline;

b. an amount of a second compound, said second compound being sodium fluoride, parathyroid hormone, growth hormone or a growth hormone secretagogues wherein the amount of the first compound alone and the amount of the second compound alone is insufficient to achieve the therapeutic effects of increase in bone formation and decrease in bone resorption if administered simultaneously and wherein the combined effect of the amounts of the first and second compounds is greater than the sum of the therapeutic effects achievable with the individual amounts of the first and second compound, and a pharmaceutically acceptable diluent or carrier.

Yet another aspect of this invention is a synergistic method for treating mammals which present with low bone mass comprising administering to a mammal having a condition which presents with low bone mass a. an amount of a first compound, said first compound being
Cis-6-(4-fluoro-phenyl)-5-[4-(2-piperidin-1-yl-ethoxy)-phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;
Cis-6-(4-hydroxyphenyl)-5-[4-(2-piperidin-1- yl-ethoxy)-phenyl]-5,6,7,8tetrahydronaphthalene-2-ol; or
1-(4'-Pyrrolidinolethoxyphenyl)-2-phenyl-6-hydroxy-1,2,3,4-tetrahydroisoquinoline; and b. an amount of a second compound, said second compound being sodium fluoride, parathyroid hormone, growth hormone or a growth hormone secretagogue wherein the amount of the first compound alone and the amount of the second compound alone is insufficient to achieve the therapeutic effects of increase in bone formation and decrease in bone resorption if administered simultaneously and wherein the combined effect of the amounts of the first and second compounds is greater than the sum of the therapeutic effects achievable with the individual amounts of the first and second compound, and a pharmaceutically acceptable diluent or carrier.

Yet another aspect of this invention is a kit containing a treatment for a condition which presents with low bone mass comprising:

a. a therapeutically effective amount of
Cis-6-(4-fluoro-phenyl)-5-[4-(2-piperidin-1-yl-ethoxy)-phenyl]-5,6,7,8-tetrahydronaphthalene-2-ol;
(−)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthalene-2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;
Cis-6-(4-hydroxyphenyl)-5-[4-(2-piperidin-1-yl-ethoxy)-phenyl]-5,6,7,8-tetrahydronaphthalene-2-ol; or
1-(4'-Pyrrolidinolethoxyphenyl)-2-phenyl-6-hydroxy-1,2,3,4-tetrahydroisoquinoline
and a pharmaceutically acceptable carrier in a first unit dosage form;

b. a therapeutically effective amount of sodium fluoride, parathyroid hormone, growth hormone or a growth hormone secretagogue and a pharmaceutically acceptable carrier in a second unit dosage form; and c. container means for containing said first and second dosage forms.

Yet another aspect of this invention is a pharmaceutical composition comprising:

a. a therapeutically effective amount of a first compound, said first compound being raloxifene, tamoxifen or idoxifene, and b. a therapeutically effective amount of a second compound, said second compound being a parathyroid hormone, growth hormone or a growth hormone secretagogue.

Yet other aspects of this invention are methods of treatment synergistic compositions and kits of the immediately preceding composition.

Those skilled in the art will recognize that other anti-resorptive agents (bisphosphonate, estrogen, estradiol, premarin, eston, estriol or 17α- or 17β-ethynyl estradiol) and other bone anabolic agents (androgen, androgen agonist/antagonist) may be used together or with any of the agents described herein in this invention in an analogous manner.

For example, the anti-resorptive agent droloxifene may be combined with an individual bone anabolic agent such as parathyroid hormone, growth hormone or growth hormone secretagogues.

The phrase "condition which presents with low bone mass" refers to a condition where the level of bone mass is below the age specific normal as defined in standards by the World Health Organization "Assessment of Fracture Risk and its Application to Screening for Postmenopausal Osteoporosis (1994), Report of a World Health Organization Study Group. World Health Organization Technical Series-843". Childhood idiopathic and primary osteoporosis are also included. Included in the treatment of osteoporosis is the prevention or attenuation of long term complications such as curvature of the spine, loss of height, prosthetic surgery, and prevention of prostate malfunctioning. Also included is increasing the bone fracture healing rate and enhancing the rate of successful bone grafts. Also included is periodontal disease and alveolar bone loss.

The phrase "condition which presents with low bone mass" also refers to a mammal known to have a significantly higher than average chance of developing such diseases as are described above including osteoporosis (e.g., post-menopausal women, men over the age of 60, and persons being treated with drugs known to cause osteoporosis as a side effect (such as glucocorticoid)).

Those skilled in the art will recognize that the term bone mass actually refers to one mass per unit area which is sometimes (although not strictly correctly) referred to as bone mineral density.

The term "treating", "treat" or "treatment" as used herein includes preventative e.g., prophylactic) and palliative treatment.

By halo is meant chloro, bromo, iodo, or fluoro.

By alkyl is meant straight chain or branched saturated hydrocarbon. Exemplary of such alkyl groups (assuming the designated length encompasses the particular example) are methyl, ethyl, propyl, isopropyl, butyl, seo-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "pharmaceutically-acceptable anionic salt" refers to nontoxic anionic salts containing anions such as (but not limited to) chloride, bromide, iodide, sulfate, bisuifate, phosphate, acetate, maleate, fumarate, oxalate, lactate, tartrate, citrate, gluconate, methanesulfonate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The parenthetical negative or positive sign used herein in the nomenclature denotes the direction plane polarized light is rotated by the particular stereoisomer.

As used herein, the expressions "reaction-inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

The chemist of ordinary skill will recognize that certain combinations of heteroatom-containing substituents listed in this invention define compounds which will be less stable under physiological conditions (e.g. those containing acetal or animal linkages). Accordingly, such compounds are less preferred.

The pharmaceutical compositions of this invention result in a more rapid and higher magnitude bone mass gain than is achievable with the same doses of estrogen agonists/antagonists as described above alone or an agent which stimulates an increase in bone mineral density as described above alone. Thus, these combinations have a synergistic action, increasing bone mass and decreasing fracture rates to a greater extent than is achievable through use of either agent alone. This invention makes a significant contribution to the art by providing compositions and methods that increase and maintain bone mass resulting in prevention, retardation, and/or regression of osteoporosis and related bone disorders.

Other features and advantages will be apparent from the specification and claims which describe the invention.

DETAILED DESCRIPTION OF THE INVENTION

The first compound of this invention is a mammalian estrogen agonist/antagonist. Any estrogen agonist/antagonist may be used as the first compound of this invention. The term estrogen agonist/antagonist refers to compounds which bind with the estrogen receptor, inhibit bone turnover and prevent bone loss. Such activities are readily determined by those skilled in the art according to standard assays including estrogen receptor binding assays (see in Vitro Estrogen Receptor Binding Assay hereinafter), standard bone histomorphometric and densitometer methods (see Estrogen Agonist/Antagonist Protocol hereinafter, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other estrogen agonists/antagonists will be known to those skilled in the art.

A preferred estrogen agonist/antagonist is droloxifene: (phenol, 3-[1-[4[2-(dimethylamino)ethoxy]phenyl]-2-phenyl-1-butenyl]-, (E)-) and associated compounds which are disclosed in U.S. Pat. No. 5,047,431 (the disclosure of which is hereby incorporated by reference).

Another preferred estrogen agonist/antagonist is tamoxifen: (ethanamine,2-[4-(1,2-diphenyl-1-butenyl)phenoxy]-N,N-dimethyl, (Z)-2-, 2-hydroxy-1,2,3-propanetricarboxylate(1:1)) and associated compounds which are disclosed in U.S. Pat. No. 4,536,516 (the disclosure of which is hereby incorporated by reference). Another related compound is 4-hydroxy tamoxifen which is disclosed in U.S. Pat. No. 4,623,660 (the disclosure of which is hereby incorporated by reference).

Another preferred estrogen agonist/antagonist is raloxifene: (methanone,-[6-hydroxy-2-(4-hydroxyphenyl)benzo[b]thien-3-yl][4-[2-(1-piperidinyl)ethoxy]phenyl], hydrochloride) and associated compounds which are disclosed in U.S. Pat. No. 4,418,068 (the disclosure of which is hereby incorporated by reference).

Another preferred estrogen agonist/antagonist is toremifene: (ethanamine, 2-[4-(4chloro-1,2-diphenyl-1-butenyl)phenoxy]-N,N-dimethyl-, (Z)-, 2-hydroxy-1,2,3-propanetricarboxylate (1:1) and associated compounds which are disclosed in U.S. Pat. No. 4,996,225 (the disclosure of which is hereby incorporated by reference).

Another preferred estrogen agonist/antagonist is centchroman: 1-[2-[[4-(-methoxy-2,2, dimethyl-3-phenyl-chroman-4-yl)-phenoxy]-ethyl]-pyrrolidine, and associated compounds which are disclosed in U.S. Pat. No. 3,822,287 (the disclosure of which is hereby incorporated by reference).

Another preferred estrogen agonist/antagonist is idoxifene: Pyrrolidine, 1-[-[4-[[1-(4-odophenyl)-2-phenyl-1-Butenyl]phenoxy]ethyl] and associated compounds which are disclosed in U.S. Pat. No. 4,839,155 (the disclosure of which is hereby incorporated by reference).

Other preferred estrogen agonist/antagonists include compounds of the formula

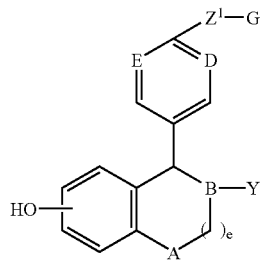

I wherein:
A is selected from $CH_2$ and NR;
B, D and E are independently selected from CH and N;
Y is
(a) phenyl, optionally substituted with 1–3 substituents independently selected from $R^4$;
(b) naphthyl, optionally substituted with 1–3 substituents independently selected from $R^4$;
(c) $C_3$-$C_8$ cycloalkyl, optionally substituted with 1–2 substituents independently selected from $R^4$;
(d) $C_3$-$C_8$ cycloalkenyl, optionally substituted with 1–2 substituents independently selected from $R^4$;
(e) a five membered heterocycle containing up to two heteroatoms selected from the group consisting of —O—, —$NR^2$— and —$S(O)_n$—, optionally substituted with 1–3 substituents independently selected from $R^4$;
(f) a six membered heterocycle containing up to two heteroatoms selected from the group consisting of —O—, —$NR^2$— and —$S(O)_n$— optionally substituted with 1–3 substituents independently selected from $R^4$; or
(g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents-independently-selected from $R^4$;
$Z^1$ is
(a) —$(CH_2)_p$ $W(CH_2)_q$—;
(b) —$O(CH_2)_p$ $CR^5R^6$—;
(c) —$O(CH_2)_p W(CH_2)_q$;
(d) —$OCHR^2CHR^3$—; or
(e) —$SCHR^2CHR^3$—;
G is
(a) —$NR^7R^8$;
(b)

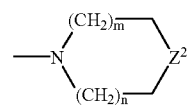

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or (c) a bicyclic amine containing five to twelve carbon atoms, either bridged or fused and optionally substituted with 1–3 substituents independently selected from $R^4$; or $Z^2$ and G in combination may be

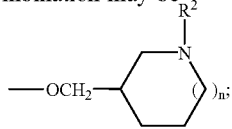

W is
(a) —$CH_2$—;
(b) —CH=CH—;
(c) —O—;
(d) —$NR^2$—;
(e) —$S(O)_n$—;
(f)

(g) —$CR^2(OH)$—;
(h) —$CONR^2$—;
(i) —$NR^2CO$—;
(j)

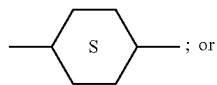

; or (k) —C≡C—;
R is hydrogen or $C_1$–$C_8$ alkyl;
$R^2$ and $R^3$ are independently
(a) hydrogen; or
(b) $C_1$–$C_4$ alkyl;
$R^4$ is
(a) hydrogen;
(b) halogen;
(c) $C_1$–$C_8$ alkyl;
(d) $C_1$–$C_4$ alkoxy;
(e) $C_1$–$C_4$ acyloxy;
(f) $C_1$–$C_4$ alkylthio;
(g) $C_1$–$C_4$ alkylsufonyl;
(h) $C_1$–$C_4$ alkylsulfonyl;
(i) hydroxy ($C_1$–$C_4$)alkyl;
(j) aryl ($C_1$–$C_4$)alkyl;
(k) —$CO_2H$;
(l) —CN;
(m) —CONHOR;
(n) —$SO_2NHR$;
(o) —$NH_2$;
(p) $C_1$–$C_4$ alkylamino;
(q) $C_1$–$C_4$ dialkylamino;
(r) —$NHSO_2R$;
(s) —$NO_2$;
(t) -aryl; or
(u) —OH;

$R^5$ and $R^8$ are independently $C_1$–$C_8$ alkyl or together form a $C_3$–$C_{10}$ carbocyclic ring;
$R^7$ and $R^8$ are independently
(a) phenyl;
(b) a $C_3$–$C_{10}$ carbocyclic ring, saturated or unsaturated;
(c) a $C_3$–$C_{10}$ heterocyclic ring containing up to two heteroatoms, selected from —O—, —N— and —S—;
(d) H;
(e) $C_1$–$C_8$ alkyl; or
(f) form a 3 to 8 membered nitrogen containing ring with $R^5$ or $R^6$;

$R^7$ and $R^8$ in either linear or ring form may optionally be substituted with up to three substituents independently selected from $C_1$–$C_8$ alkyl, halogen, alkoxy, hydroxy and carboxy;
a ring formed by $R^7$ and $R^8$ may be optionally fused to a phenyl ring;
e is 0, 1 or 2;
m is 1, 2 or 3;
n is 0, 1 or 2;
p is 0, 1, 2 or 3;
q is 0, 1, 2 or 3;
and optical and geometric isomers thereof; and nontoxic pharmacologically acceptable acid addition salts, N-oxides, esters and quaternary ammonium salts thereof.

Preferred compounds of the invention are of the formula:

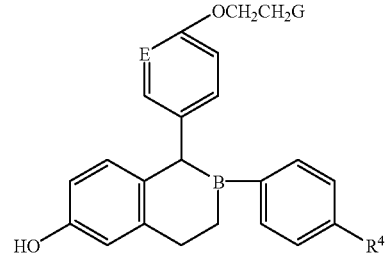

wherein G is

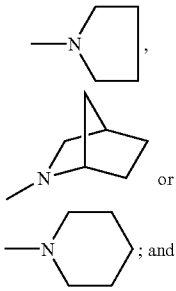

$R^4$ is H, OH, F, or Cl; and B and E are independently selected from CH and N.

Especially preferred compounds are:
Cis-6-(4-fluoro-phenyl)-5-[4-(2-piperidin-1-yl-ethoxy)-phenyl]-5,6,7,8-tetrahydronaphthalene-2-ol;
(–)-Cis-6-phenyl-5-[4-(2-pyrrolidin-1-yl-ethoxy)-phenyl]-5,6,7,8-tetrahydronaphthalene-2-ol;
Cis-6-phenyl-5-[4-(2-pyrrolidin-1-yl-ethoxy)-phenyl]-5,6,7,8-tetrahydronaphthaJene-2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydronaphthalene-2-ol; and
1-(4'-Pyrrolidinolethoxyphenyl)-2-phenylhydroxy-1,2,3,4tetrahydroisoquinoline.

The above compounds of this invention are readily prepared by the reactions illustrated in the schemes below.

Certain compounds of formula I are conveniently prepared from an unsaturated intermediate

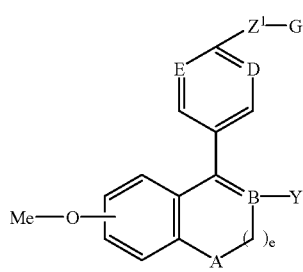

II by hydrogenation with a noble metal catalyst in a reaction inert solvent. Pressure and temperatures are not critical and hydrogenation is normally accomplished in a few hours at room temperatures at 20–80 psi hydrogen pressure.

The hydrogenated product is isolated, purified if desired, and the ether group is cleaved with an acidic catalyst in a reaction inert solvent at a temperature between 0° C. to 100° C. depending on the acidic catalyst used. Hydrogen bromide at elevated temperatures, boron tribromide and aluminum chloride at 0° C. to ambient temperature have been found to be effective for this reaction.

The product, Formula I is isolated and purified by standard procedures.

Intermediates of Formula II where A is $CH_2$, and B, D and E are CH are described in U.S. Pat. No. 3,274,213; J. Med. Chem 10, 78 (1967); J. Med. Chem 10, 138 (1967); and J. Med. Chem. 12, 881 (1969), the disclosures of which are herein incorporated by reference. They can also be prepared by procedures described below.

The preparation of the compounds of Formula I where e=1, A=$CH_2$, $Z^1$=$OCH_2CH_2$, G=cycloalkylamine, B=CH is shown in Scheme 1. Compounds 1-2, where D and E are CH are made by alkylation of 4-bromophenol with the corresponding N-chloroethytamine using potassium carbonate as base in a polar aprotic solvent like dimethylformamide at elevated temperatures. A preferred temperature is 100° C. Compounds 1-2 where D or E or both are N are synthesized using a nucleophilic displacement reaction performed on dibromides (1-1) using hydroxy ethyl cycloalkylamines under phase transfer conditions to afford bromo amines (1-2). Synthesis, 77, 673 (1980). Following halogen metal exchange using n-butyllithium or magnesium metal, bromo amines (1-2) yield the corresponding lithium or magnesium reagents which are allowed to react at low temperature in the presence of cesium chloride preferably (without cesium chloride the reaction also proceeds) with 6-methoxy-1-tetralone to afford either carbinols (1-3) or styrenes (1-4) after acidic workup. Treatment of either carbinols (1-3) or styrenes (1-4) with a brominating agent such as pyridinium bromide perbromide affords bromo styrenes (1-5). Aryl or heteroaryl zinc chlorides or aryl or heteroaryl boronic acids react with bromides (1-5) in the presence of a palladium metal catalyst like tetrakis triphenyl phosphine palladium (O) to yield diaryl styrenes (1-6). [Pure & Applied Chem. 63, 419,(1991) and Bull. Chem. Soc. Jpn. 61, 3008–3010, (1988)] To prepare the preferred compounds the substituted phenyl zinc chlorides or substituted phenylboronic acids are used in this reaction. The aryl zinc chlorides are prepared by quench of the corresponding rithium reagent with anhydrous zinc chloride. The aryl boronic acids, that are not commercially available, are prepared by quenching the corresponding aryl lithium reagent with trialkyl borate, preferably the trimethyl or triisopropyl borate, followed by aqueous acid workup. Acta Chemica Scan. 47, 221–230 (1993). The lithium reagents that are not commercially available are prepared by halogen metal exchange of the corresponding bromide or halide with n-butyl or t-butyllithium. Alternately, the lithium reagent is prepared by heteroatom facilitated lithiations as described in Organic Reactions, Volume 27, Chapter 1. Catalytic hydrogenation of 1-6 in the presence of palladium hydroxide on charcoal, for example, affords the corresponding dihydro methoxy intermediates which were subsequently demethylated using boron tribromide at 0° C. in methylene chloride or 48% hydrogen bromide in acetic acid at 80–100° C. to afford target structures (1-7). These compounds are racemic and can be resolved into the enantiomers via high pressure liquid chromatography using a column with a chiral stationary phase like the Chiralcel OD columns. Alternately optical resolution can be carried out by recrystallization of the diasereomeric salts formed with optically pure acids like 1,1'-binapthyl-2,2'-diyl hydrogen phosphate.

The cis compounds (1-7) can be isomerized to the trans compounds on treatment with base.

When D and/or E is nitrogen the intermediates (Formula II) and compounds of Formula I may be prepared from the corresponding dihalopyridines or pyrimidines as illustrated in Scheme 1.

The methyl ether of the compound of Formula I where e=1, A=$CH_2$, $Z^1$=$OCH_2CH_2$, G=pyrrolidine, D,E, B=CH, Y=Ph can also be conveniently prepared by a first step of hydrogenation of nafoxidine (Upjohn & Co., 700 Portage Road, Kalamazoo, Miss. 49001) in a reaction inert solvent in the presence of a nobel metal catalyst. Pressure and temperature are not crtical; the reaction is conveniently run in ethanol at room temperature for approximately 20 hours at 50 psi.

The second step is cleavage of the methoxy group which is accomplished conveniently at room temperature with an acidic catalyst such as boron tribromide in a reaction inert solvent or at 80–100° C. with hydrogen bromide in acetic acid. The product is then isolated by conventional methods and converted to an acid salt if desired.

SCHEME 1

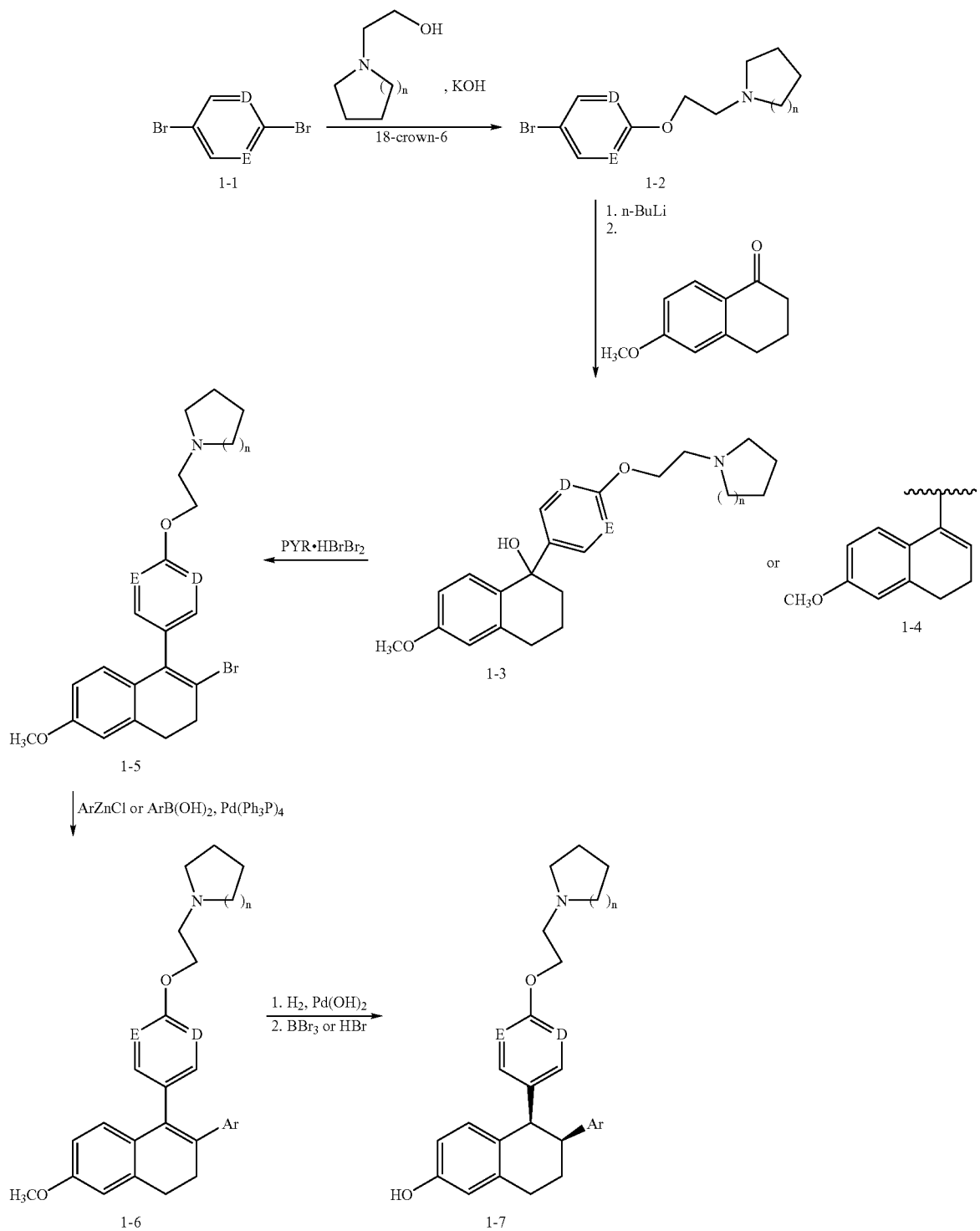

Compounds of formula I wherein B is nitrogen are prepared by the procedures illustrated in Scheme 2 and 3.

The synthesis of compounds of Formula I where B=N is shown in Scheme 2. Aryl acid chlorides (2-1) on treatment with primary amines afford aryl secondary amides (2-2), which are reduced with lithium aluminum hydride in ethereal solvents to yield secondary amines (2-3). Subsequent acylation of (2-3) with aroyl acid chlorides leads to tertiary amides (2-4), which are cyclized in hot phosphorus oxychloride to yield dihydro isoquinolinium salts (2-5). Reduction with sodium borohydride to alkoxytetrahydro isoquinolines: followed by boron tribromide demethylation in methylene chloride affords the target structures.

SCHEME 2

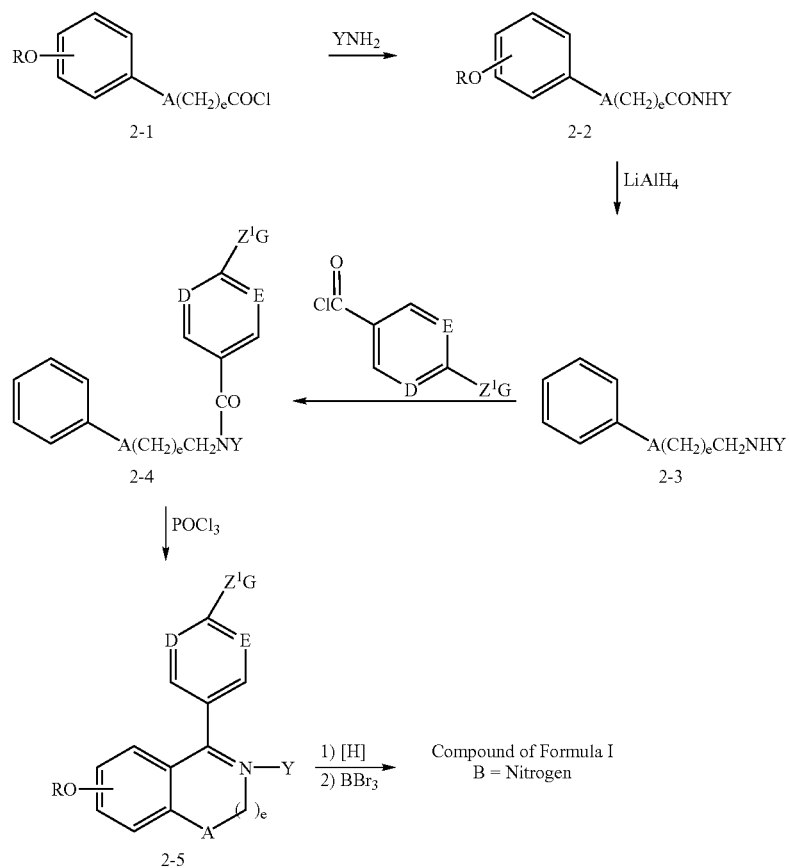

The synthesis of the compounds of Formula I where B=N is also described below in Scheme 3. Secondary amines (3-1) on acylation with benzyloxyaroyl chlorides (3-2) afford tertiary amides (3-3) which on cyclization with hot phosphorous oxychloride yield dihydro isoquinoline salts (3-4). Sodium borohydride reduction of (3-4) followed by debenzylation with aqueous hydrochloric acid affords isoquinolines (3-5), which are alkylated with the appropriately functionalized chlorides and dimethylated with boron tribromide to yield the desired target structures.

SCHEME 3

-continued

SCHEME 3

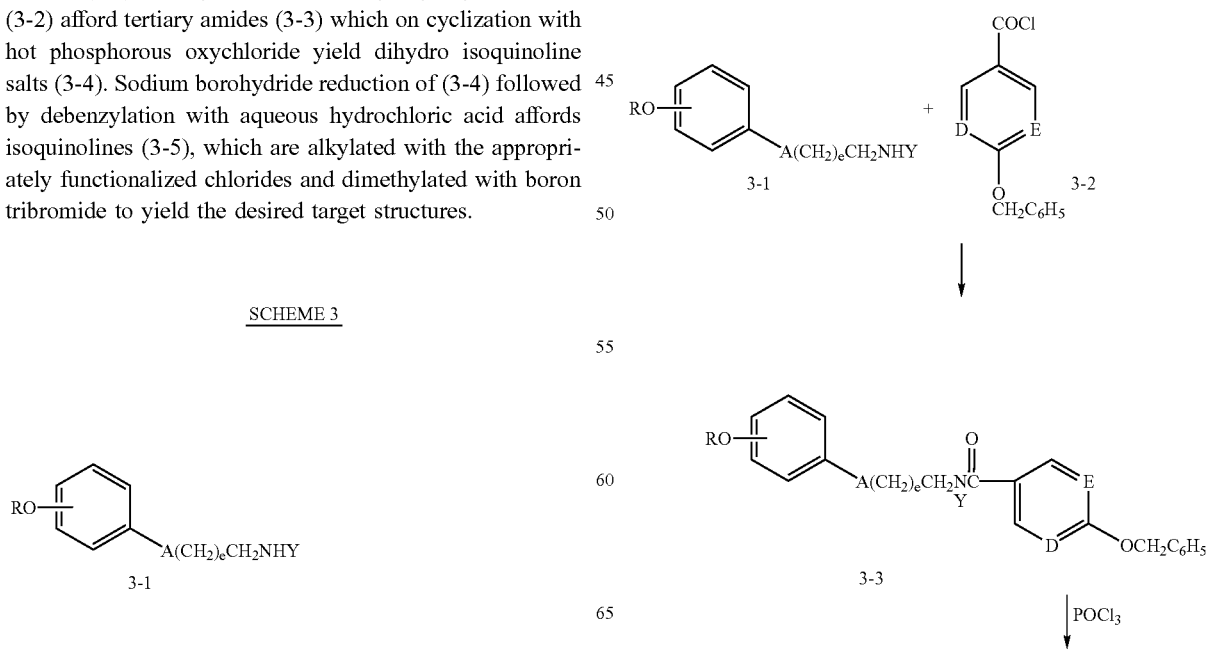

-continued

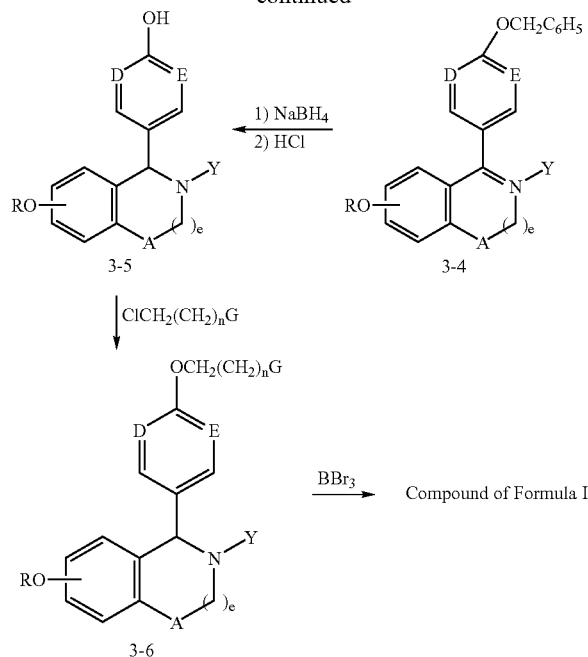

Other estrogen agonist/antagonists are described in U.S. Pat. No. 4,133,814 (the disclosure of which is hereby incorporated by reference). U.S. Pat. No. 4,133,814 discloses derivatives of 2-phenyl-3-aroyl-benzothiophene and 2-phenyl-3-aroylbenzothiophene-1-oxide.

Lednicer, et al., *J. Med. Chem.*, 12, 881 (1969) describe estrogen antagonists of the structure

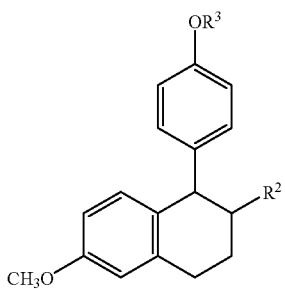

wherein $R^2$ is phenyl or cyclopentyl and $R^3$ is H,

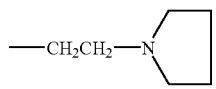

U.S. Pat. No. 3,234,090 (the disclosure of which is hereby incorporated by reference) discloses estrogen agonist/antagonist of formula

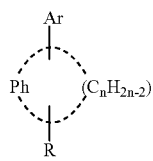

in which Ph is a 1,2-phenylene radical, Ar is a monocyclic carbocyclic aryl group substituted by tertiary amino-lower alkyl-oxy, in which tertiary amino is separated from oxy by at least two carbon atoms, R is hydrogen, an aliphatic radical, a carbocyclic aryl radical, a carbocyclic aryl-aliphatic radical, a heterocyclic aryl radical or a heterocyclic aryl aliphatic radical, the group of the formula —($C_nH_{2n-2}$)— stands for an unbranched alkylene radical having from three to five carbon atoms and carrying the groups Ar and R, salts, N-oxides, salts of N-oxides or quaternary ammonium compounds thereof, as well as a procedure for the preparation of such compounds.

U.S. Pat. No. 3,277,106 (the disclosure of which is hereby incorporated by reference) discloses basic ethers with estrogen agonist/antagonist effects which are of the formula

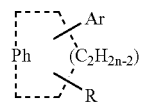

in which Ph is a 1,2-phenylene radical, Ar is a monocyclic aryl radical substituted by at least one amino-lower alkyl-oxy group in which the nitrogen atom is separated from the oxygen atom by at least two carbon atoms, R is an aryl radical, and the portion —($C_nH_{2n-2}$)— stands for lower alkylene forming with Ph a six- or seven-membered ring, two of the ring carbon atoms thereof carry the groups Ar and R, salts, N-oxides, salts of N-oxides and quaternary ammonium compounds thereof.

U.S. Pat. No. 3,274,213 (the disclosure of which is hereby incorporated by reference) discloses estrogen agonist/antagonist compounds of the formula

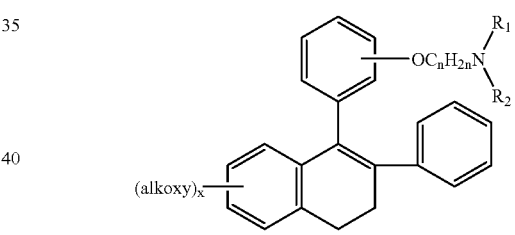

wherein $R_1$ and $R_2$ are selected from the class consisting of lower alkyl and lower alkyl linked together to form a 5 to 7 ring member saturated heterocyclic radical.

The second compound of this invention may be any compound as described below that augments bone mass to a level which is above the bone fracture threshold (as detailed in the World Health Organization Study World Health Organization, "Assessment of Fracture Risk and its Application to Screening for Postmenopausal Osteoporosis (1994). Report of a WHO Study Group. World Health Organization Technical Series 843").

Any prostaglandin, or prostaglandin agonist/antagonist may be used as the second compound of this invention. Those skilled in the at will recognize that sodium fluoride, parathyroid hormone (PTH), active fragments of parathyroid hormone, growth hormone or growth hormone secretagogues may also be used. The following paragraphs describe exemplary second compounds of this invention in greater detail.

Any prostaglandin may be used as the second compound of this invention. The term prostaglandin refers to compounds which are analogs of the natural prostaglandins $PGD_1$, $PGD_2$, $PGE_2$, $PGE_1$ and $PGF_2 \alpha$ which are useful in the treatment of osteoporosis. These compounds bind to the prostaglandin receptors. Such binding is readily determined by those skilled in the art according to standard assays (e.g., An S. et al., Cloning and Expression of the EP$_2$ Subtype of Human Receptors for Prostaglandin E$_2$, Biochemical and Biophysical Research Communications, 1993, 197(1): 263–270).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while PGE$_2$ contains a trans unsaturated double bond at the C$_{13}$–C$_{14}$ and a cis double bond at the C$_5$–C$_8$ position.

A variety of prostaglandins are described and referenced below, however, other prostaglandins will be known to those skilled in the art. Exemplary prostaglandins are disclosed in U.S. Pat. Nos. 4,171,331 and 3,927,197 (the disclosures of which we hereby incorporated by reference).

Norrdin et al., *The Role of Prostaglandins in Bone In Vivo,* Prostaglandins Leukotriene Essential Fatty Acids 41, 139–150, 1990 is a review of bone active prostaglandins.

Any prostaglandin agonist/antagonist may be used as the second compound of this invention. The term prostaglandin agonist/antagonist refers to compounds which bind to prostaglandin receptors (e.g., An S. et al., Cloning and Expression of the EP$_2$ Subtype of Human Receptors for Prostaglandin E$_2$, Biochemical and Biophysical Research Communications, 1993, 197(1):263–270) and mimic the action of prostaglandin in vivo (e.g., stimulate bone formation and increase bone mass). Such actions are readily determined by those skilled in the art according to standard assays (e.g., see Anabolic Agent Protocol described hereinafter and Erksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry In Clinical Practice., Martin Dunitz Ltd., London 1994, pages 1–296). A variety of these compounds are described and referenced below, however, other prostaglandin agonists/antagonists will be known to those skilled in the art. Exemplary prostaglandin agonists/antagonists are disclosed as follows.

Commonly assigned U.S. Pat. No. 3,932,389 (the dislosure of which is hereby incorporated by reference) discloses 2-descarboxy-2-(tetrazol-5-yl)-11-desoxy-15-substituted-omega-pentanorprostaglandins useful for bone formation activity.

Commonly assigned U.S. Pat. No. 4,018,892 (the disclosure of which is hereby incorporated by reference) discloses 16-aryl-13,14-dihydro-PGE$_2$ p-biphenyl esters useful for bone formation activity.

Commonly assigned U.S. Pat. No. 4,219,483 (the disclosure of which is hereby incorporated by reference) discloses-2,3,6-substituted-4-pyrones useful for bone formation activity.

Commonly assigned U.S. Pat. No. 4,132,847 (the disclosure of which is hereby incorporated by reference) discloses 2,3,6-substituted-4-pyrones useful for bone formation activity.

U.S. Pat. No. 4,000,309 (the disclosure of which is hereby incorporated by reference) discloses 16-aryl-13,14-dihydro-PGE$_2$ p-biphenyl esters useful for bone formation activity.

U.S. Pat. No. 3,982,016 (the disclosure of which is hereby incorporated by reference) discloses 16-aryl-13,14-dihydro-PGE$_2$ p-biphenyl esters useful for bone formation activity.

U.S. Pat. No. 4,621,100 (the disclosure of which is hereby incorporated by reference) discloses substituted cyclopentanes useful for bone formation activity.

U.S. Pat. No. 5,216,183 (the disclosure of which is hereby incorporated by reference) discloses cyclopentanones useful for bone formation activity.

Sodium fluoride may be used as the second compound of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478, the disclosure of which is hereby incorporated by reference. The activity of sodium fluoride is readily determined by those skilled in the art according to biological protocols (e.g., see Anabolic Agent Protocol described hereinafter and Eriksen E. F. et al., Bone Histomorphometry, Raven Press, New York, 1994, pages 1–74; Grier S. J. et. al., The Use of Dual-Energy X-Ray Absorptiometry in Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Lid., London 1994, pages 1–296).

Any parathyroid hormone (PTH) may be used as the second compound of this invention. The term parathyroid hormone refers to parathyrold hormone, fragments or metabolites thereof and structural analogs thereof which can stimulate bone formation and increase bone mass. Such functional activity is readily determined by those skilled in the art according to standard assays (e.g., see Anabolic Agent Protocol described hereinafter and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996,31(1): 50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1-34 Treatment of Osteoporosis with Added Hormone Replacement Therapy: Biochemical, Kinetic and Histological Responses" Osteoporosis Int. 1:162–170.

Any growth hormone or growth hormone secretagogue may be used as the second compound of this invention. The term growth hormone secretagogue refers to compounds which stimulate the release of growth hormone or mimic the action of growth hormone (e.g., increase bone formation leading to increased bone mass). Such actions are readily determined by those skilled in the art according to standard assays (e.g., as described hereinafter). A variety of these compounds are included in the following published PCT patent applications WO 95/14666; WO 95/13069; WO 94/19367; WO 94113696; and WO 95/34311. However, other growth hormone or growth hormone secretagogues will be known to those skilled in the art.

In particular a preferred growth hormone secretagogue is N-[1-(R)-[1,2-Dihydro-1-methanesulfonylspiro[3H-indole-3,4'-piperidin]-1'-yl)cabonyl]-2-(phenytmethyloxy)ethyl]-2-amino-2-methylpropanamide:MK-677.

Other preferred growth hormone secretagogues include 2-amino-N-[2-(3a-(R)-benzyl-2-methyl-3-oxo-2,3,3a,4,6,7-hexahydro-pyrazolo-[4,3-c]pyridin-5-yl)-1-(R)- benzyloxymethyl-2-oxo-ethyl]-isobutyramide or its L-tartaric acid salt;

2-amino-N-{1-(R)-benzyloxymethyl-2-[3a-(R)(4-fluorobenzyl)-2-methyl-3-oxo-2,3,3a,4,6,7-hexahydropyrazolo[4,3-c]pyridin-5yl]-2oxo-ethyl}isobutyramide; and 2-amino-N-[2-(3a-(R)-benzyl4oxo-2,3,3a,4,6,7-tetrahydropyrazolo[4,3-c]pyridin-5-yl)-1-(R)benzyloxymethyl-2-oxo-ethyl]isobutyramide.

In general, the compounds of this invention can be made by processes which include processes known in the chemical arts, particularly in light of the description contained herein.

Some of the preparation methods useful for making the compounds of this invention may require protection of remote functionality (i.e., primary amine, secondary amine, carboxyl). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*. John Wiley & Sons, New York, 1991. The starting materials and reagents for the compounds of this invention are also readily available or can be easily synthesized by those skilled in the art using conventional methods of organic synthesis. For example, many of the compounds used herein are, are related to, or are derived from compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Although many compounds of this invention are not ionizable at physiological conditions, some of the compounds of this invention are ionizable at physiological conditions. Thus, for example some of the compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds of this invention are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The pharmaceutical combinations and methods of this invention are all adapted to therapeutic use as agents that either activate bone turnover or prevent bone resorption or increase bone formation in mammals, particularly humans. Since these functions are closely related to the development of osteoporosis and bone related disorders, these combinations, by virtue of their action on bone, prevent, arrest, regress or reverse osteoporosis.

The utility of the compounds of the present invention as medical agents in the treatment of conditions which present with low bone mass (e.g., osteoporosis) in mammals (e.g. humans, particularly the female) is demonstrated by the activity of the compounds of this invention in conventional assays and the in vitro and in vivo assays described below (COMBINATION AND SEQUENTIAL TREATMENT PROTOCOL; ESTROGEN AGONIST/ANTAGONIST PROTOCOL; ANABOLIC AGENT PROTOCOL; IN VITRO ESTROGEN RECEPTOR BINDING ASSAY; AND GROWTH HORMONE/GROWTH HORMONE SECRETAGOGUE PROTOCOL). Such assays also provide a means whereby the activities of the compounds of this invention can be compared between themselves and with the activities of other known compounds. The results of these comparisons are useful for determining dosage levels in mammals, including humans, for the treatment of such diseases.

COMBINATION AND SEQUENTIAL TREATMENT PROTOCOL

The following protocols can of course be varied by those skilled in the art. For example, intact male or female rats, sex hormone deficient male (orchidectomy) or female (ovariectomy) rats may be used. In addition, male or female rats at different ages (such as 12 months of age) can be used in the studies. The rats can be either intact or castrated (ovariectomized or orchidectornized), and administrated with anabolic agents such as prostaglandin E2 (PGE2) at different doses (such as 1, 3 or 6 mg/kg/day) for a certain period (such as two weeks to two months), and followed by administration of an anti-resorptive agent such as droloxifene at different doses (such as 1,5,10 mg/kg/day) for a certain period (such as two weeks to two months), or a combination treatment with both anabolic agent and anti-resorptive agent at different doses for a certain period (such as two weeks to two months). In the castrated rats, treatment can be started at the next day after surgery (for the purpose of preventing bone loss) or at the time bone loss has already occurred (for the purpose of restoring bone mass).

The following protocols are described as using PGE2 as the bone anabolic agent and droloxifene as the antiresorptive agent, however, other anabolic agents and antiresorptive agents may be tested in the protocol.

One hundred and four female Sprague-Dawley rats (Charles River, Wilmington, Mass.) at 12 months of age are sham-operated or ovariectomized (OVX) at month 0. Three months post-surgery, OVX rats receive either Prostaglandin E$_2$ (PGE$_2$), a known anabolic bone agent, at 3 mg/kg/day (subcutaneously injection), or PGE$_2$ at 3 mg/kg/day (subcutaneously injection) combined with droloxifene (DRO) at 10 mg/kg/day (orally) for 2 months. Thereafter, the PGE$_2$ treatment is withdrawn and the rats are treated with either vehicle (10% alcohol in saline) or DRO (10 mg/kg/day, orally) for another one and a half months as described in the following.

Group I: Eight rats are autopsied at month 0 as basal controls

Group II: Eight sham-operated rats are autopsied at month 3 as pretreatment controls Group III: Eight sham-operated rats are orally treated with vehicle (10% ethanol in saline) from months 3 to 5, and autopsied at month 5.

Group IV: Eight sham-operated rats are orally treated with vehicle (10% ethanol in saline) from months 3 to 6.5, and autopsied at month 6.5.

Group V: Eight OVX rats are autopsied at month 3 as pretreatment controls

Group VI: Eight OVX rats are orally treated with vehicle (10% ethanol in saline) from months 3 to 5, and autopsied at month 5.

Group VII: Eight OVX rats are orally treated with vehicle (10% ethanol in saline) from months 3 to 6.5, and autopsied at month 6.5.

Group VIII: Eight OVX rats are subcutaneously injected with 3 mg/kg/day of PGE2 from months 3 to 5, and autopsied at month 5.

Group IX: Eight OVX rats are subcutaneously injected with 3 mg/kg/day of PGE2 from months 3 to 5, and vehicle from 5 to 6.5 months, and then autopsied at month 6.5.

Group X: Eight OVX rats are subcutaneously injected with 3 mg/kg/day of PGE2 from months 3 to 5, and 10 mg/kg/day of DRO orally from 5 to 6.5 months, and then autopsied at month 6.5.

Group XI: Eight OVX rats are subcutaneously injected with 3 mg/kg/day of PGE2 and 10 mg/kg/day of DRO orally from months 3 to 5, and then autopsied at month 5.

Group XII: Eight OVX rats are subcutaneously injected with 3 mg/kg/day of PGE2 and 10 mg/kg/day of DRO orally from months 3 to 5, and vehicle from months 5 to 6.5, then autopsied at month 6.5.

Group XIII: Eight OVX rats are subcutaneously injected with 3 mg/kg/day of PGE2 and 10 mg/kg/day of DRO orally from months 3 to 5, and DRO alone from months 5 to 6.5, then autopsied at month 6.5.

Both PGE2 (Cayman Chemical Co., Ann Arbor, Mich.) or droloxifene (Pfizer Inc. Groton, Conn.) powder are first dissolved in 100% ethanol and further diluted with saline into desired concentrations (final ethanol concentration was 10%). PGE solution is daily injected subcutaneously on the back at 1 ml/kg. Droloxifene solution is given daily p.o. at 1 ml/rat. All rats are given subcutaneous injections of 10 mg/kg kalcein (fluorochrome bone marker, Sigma Chemical Co. St. Louis Mo.) twelve and two days before death to examine the dynamic changes in bone tissues.

The rats are sacrificed under ketamine anesthesia. The following endpoints are determined:

Femoral Bone Mineral Measurements:

The right femur from each rat is removed at autopsy and scanned using dual energy xray absorptiometry (DXA, QODR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

LumbarVertebral Bone Mineral Measurements:

Dual energy xray absorptiometry (QDR 1000/W, Hologic, Inc., Waltham, Mass.) equipped with a "Regional High Resolution Scan" software (Hologic, Inc., Waltham, Mass.) is used to determined the bone area, bone mineral content (BMC), and bone mineral density (BMD) of whole lumbar spine and each of the six lumbar vertebrae (LV1-6) in the anesthetized rats. The rats are anesthetized by injection (i.p.) of 1 ml/kg of a mixture of ketamine/rompun (ratio of 4 to 3), and then placed on the rat platform. The scan field sized is 6×1.9 cm, resolution is 0.0254×0.0127 cm, and scan speed is 7.25 mm/sec. The whole lumbar spine scan image is obtained and analyzed. Bone area (BA), and bone mineral content (BMC) is determined, and bone mineral density is calculated (MBC divided by BA) for the whole lumbar spine and each of the six lumbar vertebrae (LV1–6).

Proximal Tibial Metaphyseal Cancellous Bone Histomorphometric Analyses:

The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness is cut using Reichert-Jung Polycut S microtome. One 4 μm and one 10 μm sections from each rat is used for cancellous bone histomorphometry. The 4 μm sections is stained with modified Masson's Trichrome stain while the 10 μm sections remained unstained.

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and calculations related to trabecular bone volume and structure:

1. Total metaphyseal area (TV, mm$^2$): metaphyseal area between 1.2 and 3.6 mm distal to the growth plate-epiphyseal junction.

2. Trabecular bone area (BV, mm$^2$): total area of trabeculae within TV.

3. Trabecular bone perimeter (BS, mm): the length of total perimeter of trabeculae.

4. Trabecular bone volume (BV/TV, %): BV/TV×100.

5. Trabecular bone number (TBN, #/mm): 1.199/2×BS/TV.

6. Trabecular bone thickness (TBT, μm): (2000/1.199)×(BV/BS).

7. Trabecular bone separation (TBS, μm): (2000×1.199)×(TV−BV).

II. Measurements and calculations related to bone resorption

1. Osteoclast number (OCN, #): total number of osteoclast within total metaphyseal area.

2. Osteoclast perimeter (OCP, mm): length of trabecular perimeter covered by osteoclast.

3. Osteoclast number/mm (OCN/mm, #/mm): OCN/BS.

4. Percent osteoclast perimeter (% OCP, %): OCP/BS×100.

III. Measurements and calculations related to bone formation and turnover:

1. Single-calcein labeled perimeter (SLS, mm): total length of trabecular perimeter labeled with one calcein label.

2. Double-calcein labeled perimeter (DLS, mm): total length of trabecular perimeter labeled with two calcein labels.

3. Inter-labeled width (ILW, μm): average distance between two calcein labels.

4. Percent mineralizing perimeter (PMS, %): (SLS/2+DLS)/BS×100.

5. Mineral apposition rate (MAR, μm/day): ILW/label interval.

6. Bone formation rate/surface ref. (BFR/BS, μm²/d/μm): (SLS/2+DLS)×MAR/BS.

7. Bone turnover rate (BTR, %/y): (SLS/2+DLS)×MAR/BV×100.

Statistics

Statistics can be calculated using StatView 4.0 packages (Abacus Concepts, Inc., Berkeley, Calif.). The analysis of variance (ANOVA) test followed by Fisher's PLSD can be used to compare the differences between groups.

ESTROGEN AGONIST/ANTAGONIST PROTOCOL

Estrogen agonist/antagonists are a class of compounds which inhibits bone turnover and prevents estrogen deficiency induced bone loss. The ovariectomized rat bone loss model has been widely used as a model of postmenopausal bone loss. Using this model, one can test the efficacy of the estrogen agonist/antagonist compounds in preventing bone loss and inhibiting bone resorption.

Sprague-Dawley female rats (Charles River, Wilmington, Mass.) at different ages (such as 5 months of age) are used in these studies. The rats are singly housed in 20 cm×32 cm×20 cm cages during the experimental period. All rats are allowed free access to water and a pelleted commercial diet (Agway ProLab 3000, Agway County Food, Inc., Syracuse, N.Y.) containing 0.97% calcium, 0.85% phosphorus, and 1.05 IU/g of Vdt.$D_3$ A group of rats (8 to 10) are sham-operated and treated p.o. with vehicle (10% ethanol and 90% saline, 1 ml/day), while the remaining rats are bilaterally ovariectomized (OVX) and treated with either vehicle (p.o.), 17β-estradiol (Sigma, E-8876, $E_2$, 30 μg/kg, daily subcutaneous injection), or estrogen agonist/antagonists (such as droloxifene at 5, 10, or 20 mg/kg, daily p.o.) for a certain period (such as 4 weeks). All rats are given subcutaneous injections of 10 mg/kg calcein (fluorochrome bone marker) 12 and 2 days before being sacrificed in order to examine the dynamic changes in bone tissue. After 4 weeks of treatment, the rats are autopsied. The following endpoints are determined:

Body Weight Gain:

body weight at autopsy minus body weight at surgery.

Uterine Weight and Histology:

The uterus is removed from each rat during autopsy, and weighed immediately. Thereafter, the uterus is processed for histologic measurements such as uterine cross-sectional tissue area, stromal thickness, and luminal epithelial thickness.

Total Serum Cholesterol:

Blood is obtained by cardiac puncture and allowed to clot at 4° C., and then centrifuged at 2,000 g for 10 min. Serum samples are analyzed for total serum cholesterol using a high performance cholesterol calorimetric assay (Boehringer Mannheim Biochemicals, Indianapolis, Ind.).

Femoral Bone Mineral Measurements:

The right femur from each rat is removed at autopsy and scanned using dual energy x-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) is determined Proximal Tibial Metaphyseal Cancellous Bone Histomorphometric Analyses:

The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness are cut using Reicher-Jung Polycut S microtome. One 4 μm and one 10 μm sections from each rat are used for cancellous bone histomorphometry. The 4 μm sections are stained with modified Masson's Trichrome stain while the 10 μm sections remained unstained.

A Bioquant OS/2 histomorphometry system (R&M biometrics, Inc., Nashville, Tenn.) is used for the static and dynamic histomorphometric measurements of the secondary spongiosa of the proximal tibial metaphyses between 12 and 3.6 mm distal to the growth plate-epiphyseal junction. The first 12 mm of the tibial metaphyseal region is omitted in order to restrict measurements to the secondary spongiosa The 4 μm sections are used to determine indices related to bone volume, bone structure, and bone resorption, while the 10 μm sections are used to determine indices related to bone formation and bone turnover.

I. Measurements and calculations related to trabecular bone volume and structure:

1. Total metaphyseal area (TV, mm²): metaphyseal area between 1.2 and 3.6 mm distal to the growth plate epiphyseal junction.

2. Trabecular bone area (BV, mm²): total area of trabeculae within TV.

3. Trabecular bone perimeter (BS, mm): the length of total perimeter of trabeculae.

4. Trabecular bone volume (BV/TV, %): BV/TV×100.

5. Trabecular bone number (TBN, #/mm): 1.199/2×BS/TV.

6. Trabecular bone thickness (TBT, μm): (2000/1.199)×(BV/BS).

7. Trabecular bone separation (TBS, μm): (2000×1.199)×(TV−BV).

II. Measurements and calculations related to bone resorption:

1. Osteoclast number (OCN, #): total number of osteoclast within total metaphyseal area.

2. Osteoclast perimeter (OCP, mm): length of trabecular perimeter covered by osteoclast.

3. Osteoclast number/mm (OCN/mm, #/mm): OCN/BS.

4. Percent osteoclast perimeter (% OCP, %): OCP/BS×100.

III. Measurements and calculations related to bone formation and turnover:

1. Single-calcein labeled perimeter (SLS, mm): total length of trabecular perimeter labeled with one calcein label.

2. Double-calcein labeled perimeter (DLS, mm): total length of trabecular perimeter labeled with two calcein labels.

3. Inter-labeled width (ILW, μm): average distance between two calcein labels. 4. Percent mineralizing perimeter (PMS, %): (SLS/2+DLS)/BS×100.

5. Mineral apposition rate (MAR, μm/day): ILW/label interval.

6. Bone formation rate/surface ref. (BFR/BS, μm²/d/μm): (SLS/2+DLS)×MAR/BS.

7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fisher's PLSD is used to compare the differences between groups.

ANABOLIC AGENT PROTOCOL

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) are used in the study. The rats are either intact or castrated (ovariectomized or orchidectomized), and subcutaneously injected or orally treated with anabolic agents such as prostaglandin E2 (PGE2) at different doses (such as 1, 3, or 6 mg/kg/day) for certain periods (such as 2 weeks to 2 months). In the castrated rats, treatment is started at the next day after surgery (for the purpose of preventing bone loss) or at the time bone loss has already occurred (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vit.$D_3$. All rats are given subcutaneous injections of 10 mg/kg calcein on days 12 and 2 before sacrifice.

The rats are sacrificed. The following endpoints are determined:

Femoral Bone Mineral Measurements:

The right femur from each rat is removed at autopsy and scanned using dual energy x-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area. bone mineral content (BMC), and bone mineral density (BMD) of whole femora (WF), distal femoral metaphyses PFM), femoral shaft (FS), and proximal femora (PF) are determined Proximal Tibial Metaphvseal Cancellous Bone Histomorphometric Analyses:

The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness are cut using Relchert-Jung Polycut S microtome. One 4 μm and one 10 μm sections from each rat are used for cancellous bone histomorphometry. The 4 μm sections are stained with modified Masson's Trichrome stain while the 10 μm sections remained unstained.

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region are omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and calculations related to trabecular bone volume and structure:

1. Total metaphyseal area (TV, mm²): metaphyseal area between 1.2 and 3.6 mm distal to the growth plate-epiphyseal junction.

2. Trabecular bone area (BV, mm²): total area of trabeculae within TV.

3. Trabecular bone perimeter (BS, mm): the length of total perimeter of trabeculae.

4. Trabecular bone volume (BV/TV, %): BV/TV×100.

5. Trabecular bone number (TBN, #/mm): 1.199/2×BS/TV.

6. Trabecular bone thickness (TBT, μm): (2000/1.199)×(BV/BS).

7. Trabecular bone separation (TBS, μm): (2000×1.199)×(TV−BV).

II. Measurements and calculations related to bone resorption:

1. Osteoclast number (OCN, #): total number of osteoclast within total metaphyseal area.

2. Osteoclast perimeter (OCP, mm): length of trabecular perimeter covered by osteoclast.

3. Osteoclast number/mm (OCN/mm, #/mm): OCN/BS.

4. Percent osteoclast perimeter (% OCP, %): OCP/BS×100.

III. Measurements and calculations related to bone formation and turnover:

1. Single-calcein labeled perimeter (SLS, mm): total length of trabecular perimeter labeled with one calcein label.

2. Double-calcein labeled perimeter (DLS, mm): total length of trabecular perimeter labeled with two calcein labels.

3. Inter-labeled width (ILW, μm): average distance between two calcein labels.

4. Percent mineralizing perimeter (PMS, %): (SLS/2+DLS)/BS×100.

5. Mineral apposition rate (MAR, μm/day): ILW/label Interval.

6. Bone formation rate/surface ref. (BF/RIBS, μm²/d/μm): (SLS/2+DLS)×MAR/BS.

7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fishers PLSD is used to compare the differences between groups.

IN VITRO ESTROGEN RECEPTOR BINDING ASSAY

An in vitro estrogen receptor binding assay, which measures the ability of the estrogen agonist/antagonist compounds of the present invention to displace [3H]-estradiol from human estrogen receptor obtained by recombinant methods in yeast, is used to determine the estrogen receptor binding affinity of the compounds of this invention. The materials used in this assay are: (1) Assay buffer, TD-0.3 (containing 10 Nm Tris, pH 7.6, 0.3 M potassium chloride and 5 mM Dithiothreitol (DTT) (Sigma Co.), pH 7.6); (2) The radioligand used is [3H]-estradiol obtained from New England Nuclear; (3) the cold ligand used is estradiol obtained from Sigma (4) recombinant human estrogen receptor, hER.

A solution of the compound being tested is prepared in TD-0.3 with 4% DMSO and 16% ethanol. The tritiated estradiol is dissolved in TD-0.3 such that the final concentration in the assay is 5 nM. The hER is also diluted with TD-0.3 such that 4–10 µg of total protein is in each assay well. Using microtitre plates, each incubate receives 50 ul of cold estradiol (nonspecific binding) or the compound solution, 20 uL of the tritiated estradiol and 30 ul of hER solutions. Each plate contains in triplicate total binding and varying concentrations of the compound. The plates are incubated overnight at 4° C. The binding reaction is then terminated by the addition and mixing of 100 mL of 3% hydroxylapatite in 10 mM tris, pH 7.6 and incubation for 15 minutes at 4° C. The mixtures are centrifuged and the pellet washed four times with 1% Triton-X100 in 10 mM Tris, pH 7.6. The hydroxylapatite pellets are suspended in Ecoscint A and radioactivity is assessed using beta scintigraphy. The mean of all triplicate data points (counts per minute, cpm's) is determined. Specific binding is calculated by subtracting nonspecific cpm's (defined as counts that remain following separation of reaction mixture containing recombinant receptor, radioligand, and excess unlabeled ligand) from total bound cpm's (defined as counts that remain following the separation of reaction mixture containing only recombinant receptor, radioligand). Compound potency is determined by means of IC50 determinations (the concentration of a compound needed to inhibition 50% of the of the total specific trtiated estradiol bound). Specific binding in the presence of varying concentrations of compound is determined and calculated as percent specific binding of total specific radioligand bound. Data are plotted as percent inhibition by compound (linear scale) versus compound concentration (log scale).

GROWTH HORMONE/GROWTH HORMONE SECRETAGOGUE PROTOCOL

Compounds that have the ability to stimulate GH secretion from cultured rat pituitary cells are identified using the following protocol. This test is also useful for comparison to standards to determine dosage levels. Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P-6141) in HBSS. The tissue-enzyme mixture is stirred in a spinner flask at 30 rpm in a 5% CO2 atmosphere at about 37° C. for about 30 min, with manual trituration after about 15 min and about 30 min using a 10 mL pipet. This mixture is centrifuged at 200×g for about 5 min. Horse serum is added to the supernatant to neutralize excess protease. The pellet is resuspended in fresh protease, stirred for about 30 min more under the previous conditions, and manually triturated, ultimately through a 23-gauge needle. Again, horse serum is added, then the cells from both digests are combined, pelleted (200×g for about 15 min), washed, resuspended in culture medium and counted. Cells are plated at 6.0–6.5×10⁴ cells per cm² in 48-well Costar dishes and cultured for 3–4 days in Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentarnycin sulfate before assaying for GH secretion.

Just prior to assay, culture wells are rinsed twice, then equilibrated for about 30 minutes in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the culture medium, which is centrifuged at 2000×g for about 15 minutes to remove cellular material. Rat growth hormone concentrations in the supernatants are determined by a standard radioimmunoassay protocol using a rat growth hormone reference preparation (NIDDK-rGH-RP-2) and rat growth hormone antiserum raised in monkey (NlDDK-anti-rGH-S-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 µCi/µg by the chloramine T method for use as tracer. Immune complexes are obtained by adding goat antiserum to monkey IgG (Organon Teknika, Durham, N.C.) plus polyethylene glycol, MW 10,000–20,000 to a final concentration of 4.3%; recovery is accomplished by centrifugation. This assay has a working range of 0.08–2.5 µg rat growth hormone per tube above basal levels. Active compounds typically stimulate growth hormone release by greater than 1.4 fold. Reference: Cheng, K, Chan, W.-S., Barreto, Jr., A., Convey, E. M., Smith, R. G. 1989.

Assay for Exogenously-Simulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad libitum.

On the day of the experiment, test compounds are dissolved in vehicle containing 1% ethanol, 1 mM acetic acid and 0.1% bovine serum albumin in saline. Each compound is tested with n=3. Rats are weighed and anesthetized via intraperitoneal injection of sodium pentobarbftal (Nembutol, 50 mg/kg body weight). Fourteen minutes after anesthetic administration, a blood sample is taken by nicking the tip of the tall and allowing the blood to drip into a microcentrifuge tube (baseline blood sample, approximately 100 µl). Fifteen minutes after anesthetic administration, test compound is delivered by intravenous injection into the tail vein, with a total injection volume of 1 ml/kg body weight. Additional blood samples are taken from the tail at 5, 10 and 15 minutes after compound administration. Blood samples are kept on ice until serum separation by centrifugatlon (1430×g for 10 minutes at 10° C.). Serum is stored at −80° C. until serum growth hormone determination by radioimmunoassay as described above and below.

Assessment of Exogenously-Stimulated Growth Hormone Release in the Dog after Oral Administration On the day of experimentation, the test compound is weighed out for the appropriate dose and dissolved in water. Doses are delivered at a volume of 0.5 ml/kg by gavage to 4 dogs for each dosing regimen. Blood samples (2 ml) are collected from the jugular vein by direct vena puncture pro-dose and at 0.08, 0.17, 0.25, 0.5, 0.75, 1, 2, 4, 6, and 8 hours post dose using 2 ml vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A Parlow (HarborUCLA Medical Center, Torrence, Calif.). Tracer is produced by chloramine Tiodination of canine growth hormone to a specific activity of 20–40 µCi/µg. Immune complexes are obtained by adding goat antiserum to monkey IgG (Organon Teknika, Durham, N.C.) plus polyethylene glycol, MW 10,000–20,000 to a final concentration of 4.3%; recovery is accomplished by centrifugation. This assay has a working range of 0.08–2.5 µg canine GH/tube.

Administration of the compounds of this invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. The two different compounds of this invention can be co-administered simultaneously or sequentially in any order, or a single pharmaceutical composition comprising a first compound as described above and a second compound as described above in a pharmaceutically acceptable carrier can be administered.

For example, the bone anabolic agent can be used alone or in combination with an antiresorptive agent for three months to three years, followed by an anti-resorptive agent alone for three months to three years, with optional repeat of the full treatment cycle. Alternatively, for example, the bone anabolic agent can be used alone or in combination with an anti-resorptive agent for three months to three years, followed by an anti-resorptive agent alone for the remainder of the patients life. For example, in one preferred mode of administration a second compound as described above (e.g., PGE$_2$) may be administered once daily and a first compound as described above (e.g., estrogen agonist/antagonist) may be administered daily in single or multiple doses. Alternatively, for example, in another preferred mode of administration the two compounds may be administered sequentially wherein the second compound as described above (e.g., PGE$_2$) may be administered once daily for a period of time sufficient to augment bone mass to a level which is above the bone fracture threshold (World Health Organization Study "Assessment of Fracture Risk and its Application to Screening for Postmenopausal Osteoporosis (1994). Report of a World Health Organization Study Group. World Health Organization Technical Series 843") followed by administration of a first compound, as described above (e.g., estrogen agonist/antagonist), daily in single or multiple doses. It is preferred that the second compound as described above (e.g., PGE$_2$) is administered once daily in a rapid delivery form such as oral delivery (e.g., sustained release delivery form is preferably avoided).

In any event the amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the activity (e.g., bone mass augmentation) that the physician considers appropriate for the individual patient. In considering the degree of activity desired, the physician must balance a variety of factors such as bone mass starting level, age of the patient, presence of preexisting disease, as well as presence of other diseases (e.g., cardiovascular). For example, the administration of an estrogen agonist/antagonist can provide cardiovascular benefits particularly, for post-menopausal women. The following paragraphs provide preferred dosage ranges for the various components of this invention.

The amount of the antresorptive agent to be used is determined by its activity as a bone loss inhibiting agent. This activity is determined by means of an individual compound's pharmacokinetics and its minimal maximal effective dose in inhibition of bone loss using a protocol as described above (ESTROGEN AGONIST/ANTAGONIST PROTOCOL).

In general an effective dosage for the activities of this invention, for example the bone resorption activities of this invention, for the first compounds of this invention is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for

Cis-6-(4-fluoro-phenyl)-5-[4-(2-piperidin-1-yl-ethoxy)-phenyl]-5,6,7,8-tetrahydronaphthalene-2-ol;

(−)-Cis-6-phenyl-5-[4-(2-pyrrolidin-1-yl-ethoxy)-phenyl]-5,6,7,8-tetrahydronaphthalene-2-ol;

Cis-6-phenyl-5-[4-(2-pyrrolidin-1-yl-ethoxy)-phenyl]-5,6,7,8-tetrahydronaphthalene-2-ol;

Cis-1-[6'-pyrrolodinoethoxy-3'-pyridyl]-2-phenyl-6-hydroxy-1,2,3,4-tetrahydrohaphthalene:

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1yl-ethoxy)-phenyl]-5,6,7,8-tetrahydronaphthalene-2-ol; or 1-(4'-Pyrrolidinolethoxyphenyl)-2-phenyl-6-hydroxy-1,2,3,4-tetrahydroisoquinoline. is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

In general an amount of a bone anabolic agent (e.g., PGE$_2$) is used that is sufficient to augment bone mass to a level which is above the bone fracture threshold (as detailed in the World Health Organization Study previously cited herein).

In general an effective dosage for the bone anabolic agent described above is in the range of 0.001 to 100 mg/kg/day, preferably 0.1 to 10 mg/kg/day.

In particular, an effective dosage for PGE$_2$ is in the range of 0.001 to 10 mg/kg/day, preferably 0.01 to 1 mg/kg/day.

In particular, an effective dosage for 3S-(3-Hydroxphenyl-butyl)-2R-[6-(2H-tetrazol-5-yl)-hexyl]-cyclopentanone is in the range of 0.001 to 20 mg/kg/day, preferably 0.01 to 10 mg/kg/day.

In particular, an effective dosage for sodium fluoride is in the range of 0.01 to 50 mg/kg/day, preferably 0.2 to 10 mg/kg/day.

In particular, an effective dosage for a parathyroid hormone and metabolites and fragments thereof is in the range of 0.00001 mg/kg/day to 1 mg/kg/day, preferably 0.001 to 0.5 mg/kg/day.

In particular, an effective dosage for growth hormone or growth hormone secretagogues is in the range of 0.0001 to 100 mg/kg/day, preferably 0.01 to 5 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated.

Since the present invention relates to the augmentation and maintenance of bone mass by treatment with a combination of active ingredients which may be administered separately, the invention also relates to combining separate pharmaceutical compositions in kit form. The kit includes two separate pharmaceutical compositions: an estrogen agonist/antagonist and an anabolic agent. The kit includes container means for containing the separate compositions such as a divided bottle or a divided foil packet. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a memory aid on the card, e.g., in the form of numbers next to the tablets or capsules whereby the numbers correspond with the days of the regimen which the tablets or capsules so specified should be ingested. Another example of such a memory aid is a calendar printed on the card e.g., as follows "First Week, Monday, Tuesday, . . . etc . . . . Second Week, Monday, Tuesday , . . . " etc. Other variations of memory aids will be readily apparent. A "daily dose" can be a single tablet or capsule or several pills or capsules to be taken on a given day. Also a daily dose of bone anabolic agent can consist of one tablet or capsule while a daily dose of a anti-resorptive agent can consist of several tablets or capsules. The memory aid should reflect this.

In another specific embodiment of the invention a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

EXAMPLE

One hundred and four female Sprague-Dawley rats (Charles River, Wilmington, Mass.) at 12 months of age were sham-operated or ovariectomized (OVX) at month 0. Three months post-surgery, OVX rats were treated with either Prostaglandin $E_2$ ($PGE_2$), a known anabolic bone agent, at 3 mg/kg/day (subcutaneously injection), or $PGE_2$ at 3 mg/kg/day (subcutaneously injection) combined with droloxifene (DRO) at 10 mg/kg/day (orally) for 2 months. Thereafter, the $PGE_2$ treatment was withdrawn and the rats were then treated with either vehicle (10% alcohol in saline) or DRO (10 mg/kg/day, orally) for another one and a half months as described in the following.

Group I: Eight rats were autopsied at month 0 as basal controls.

Group II: Eight sham-operated rats were autopsied at month 3 as pre-treatment controls.

Group III: Eight sham-operated rats were orally treated with vehicle (10% ethanol in saline) from months 3 to 5, and autopsied at month 5.

Group IV: Eight sham-operated rats were orally treated with vehicle (10% ethanol in saline) from months 3 to 6.5, and autopsied at month 6.5.

Group V: Eight OVX rats were autopsied at month 3 as pre-treatment controls.

Group VI: Eight OVX rats were orally treated with vehicle (10% ethanol in saline) from months 3 to 5, and autopsied at month 5.

Group VII: Eight OVX rats were orally treated with vehicle (10% ethanol in saline) from months 3 to 6.5, and autopsied at month 6.5.

Group VIII: Eight OVX rats were subcutaneously injected with 3 mg/kg/day of $PGE_2$ from months 3 to 5, and autopsied at month 5.

Group IX: Eight OVX rats were subcutaneously injected with 3 mg/kg/day of PGE2 from months 3 to 5, and vehicle from 5 to 6.5 months, and then autopsied at month 6.5.

Group X: Eight OVX rats were subcutaneously injected with 3 mg/kg/day of $PGE_2$ from months 3 to 5, and 10 mg/kg/day of DRO orally from 5 to 6.5 months, and then autopsied at month 6.5.

Group XI: Eight OVX rats were subcutaneously injected with 3 mg/kg/day of $PGE_2$ and 10 mg/kg/day of DRO orally from months 3 to 5, and then autopsied at month 5.

Group XII: Eight OVX rats were subcutaneously injected with 3 mg/kg/day of $PGE_2$ and 10 mg/kg/day of DRO orally from months 3 to 5, and vehicle from months 5 to 6.5, then autopsied at month 6.5.

Group XIII: Eight OVX rats were subcutaneously injected with 3 mg/kg/day of $PGE_2$ and 10 mg/kg/day of DRO orally from months 3 to 5, and DRO alone from months 5 to 6.5, then autopsied at month 6.5.

Both $PGE_2$ (Cayman Chemical Co., Ann Arbor, Mich.) or droloxifene (Pfizer Inc. Groton, Conn.) powder was first dissolved in 100% ethanol and further diluted with saline into desired concentrations (final ethanol concentration was 10%). A $PGE_2$ solution was daily injected subcutaneously on the back at 1 ml/kg. A droloxifene solution was given daily p.o. at 1 ml/rat.

Lumbar Vertebral Bone Mineral Measurements

Dual energy x-ray absorptiometry (QDR 1000/W, Hologic, Inc., Waltham, Mass.) equipped with a "Regional High Resolution Scan" software (Hologic, Inc., Waltham, Mass.) was used to determined the bone area, bone mineral content (BMC), and bone mineral density (BMD) of whole lumbar spine and each of the six lumbar vertebrae (LV1–6) in the anesthetized rats. The rats were anesthetized by injection (i.p.) of 1 ml/kg of a mixture of ketamine/rompun (ratio of 4 to 3), and then placed on the rat platform. The scan field sized was 6×1.9 cm, resolution was 0.0254× 0.0127 cm, and scan speed was 7.25 mm/sec. The whole lumbar spine scan image was obtained and analyzed. Bone area (BA), and bone mineral content (BMC) were determined, and bone mineral density was calculated (MBC divided by BA) for the whole lumbar spine and each of the six lumbar vertebrae (LV1–6).

At 3, 5, or 6.5 months post-surgery, BMC and BMD of whole lumbar spine and each of the lumbar vertebrae was significantly decreased by 15% to 27% in OVX rats compared to sham controls. Rats 3 months post-OVX treated with either $PGE_2$ alone or combined with DRO for 2 months had completely restored BMC and BMD back to the sham control levels. There was no difference in BMC and BMD of OVX rats treated with $PGE_2$ alone or $PGE_2$ combined with DRO, indicating that DRO did not blunt the anabolic effects of $PGE_2$. Upon $PGE_2$ cessation of treatment, a significant decrease in BMD of LV1, LV2, and LV3, and in BMC of LV2 was observed. On the other hand, when DRO treatment was given to these OVX rats after discontinuation of $PGE_2$, the $PGE_2$-restored bone was completely maintained. Similarly, discontinuation of both $PGE_2$ and DRO for 1.5 months produced a significant decrease in BMD of LV3. However, when $PGE_2$ was withdrawn and DRO treatment was continued for another 1.5 months, no bone loss was found in the lumbar spine of these OVX rats. We concluded that DRO, an anti-resorptive agent, did not blunt the anabolic effects of $PGE_2$ in osteogenic rats. Further, DRO was efficacious in maintaining $PGE_2$-restored bone after discontinuation of $PGE_2$. These data support the strategy of using an anabolic agent to restore bone mass in the osteoporotic skeleton followed by an anti-resorptive agent to maintain the restored bone mass.

It should be understood that the invention is not limited to the particular embodiments described herein, but that various changes and modifications may be made without departing from the spirit and scope of this novel concept as defined by the following claims.

What is claimed is:

1. A pharmaceutical composition comprising:
   a. a therapeutically effective amount of a first compound, said first compound being an estrogen agonist/antagonist; and
   b. a therapeutically effective amount of a second compound, said second compound being a prostaglandin or a prostaglandin agonist/antagonist. and a pharmaceutical carrier; wherein the estrogen agonist/antagonist is droloxifene, raloxifene, tamoxifen, 4-hydroxy-tamoxifen,
   Cis-6-(4-fluoro-phenyl)-5-[4-(2-piperidin-1-yl-ethoxy) phenyl]-5,6,7,8-tetrahydro-naphthalene-2-ol;
   (−)-Cis-6-phenyl-5-[4-(2-pyrrolidin-1-yl-ethoxy)- phenyl]-5,6,7,8-tetrahydro-naphthalene-2-ol;
   Cis-6-phenyl-5-[4-(2-pyrrolidin-1-yl-ethoxy)-phenyl]-5, 6,7,8-tetrahydro-naphthalene-2-ol;
   Cis-1-[6'-pyrrolodinoethoxy-3'-pyridyl]-2-phenyl-6- hydroxy-1,2,3,4-tetrahydronaphthalene;
   1-(4'-Pyrrolidinoethoxyphenyl)-2-(4"-fluorophenyl)-6- hydroxy-1,2,3,4-tetrahydroisoquinoline;
   Cis-6-(4-hydroxyphenyl)-5-[4-(2-piperidin-1-yl-ethoxy)- phenyl]-5,6,7,8-tetrahydro-naphthalene-2-ol; or
   1-(4'-Pyrrolidinolethoxyphenyl)-2-phenyl-6-hydroxy-1, 2,3,4-tetrahydroisoquinoline.

2. A pharmaceutical composition according to claim 1 wherein the second compound is $PGD_1$, $PGD_2$, $PGE_2$, $PGE_1$, $PGF_2$, $PGF_2\alpha$ or 3S-(3-Hydroxy-4-phenyl-butyl)- 2R-[6-(1H-tetrazol-5-yl)-hexyl]-cyclopentanone.

3. A pharmaceutical composition according to claim 2 wherein the second compound is $PGE_2$.

4. A pharmaceutical composition according to claim 2 wherein the second compound is 3S-(3-Hydroxy-4-phenyl- butyl)-2R-[6-(2H-tetrazol-5-yl)-hexyl]-cyclopentanone.

5. A pharmaceutical composition according to claim 2 wherein the estrogen agonist/antagonist is
   Cis-6-(4-fluoro-phenyl)-5-[4-(2-piperidin-1-yl-ethoxy)- phenyl]-5,6,7,8-tetrahydro-naphthalene-2-ol;

(−)-Cis-6-phenyl-5-[4-(2-pyrrolidin-1-yl-ethoxy)-phenyl]-5,6,7,8-tetrahydro-naphthalene-2-ol;

Cis-6-phenyl-5-[4-(2-pyrrolidin-1-yl-ethoxy)-phenyl]-5,6,7,8-tetrahydro-naphthalene2-ol;

Cis-1-[6'-pyrrolodinoethoxy-3'-pyridyl]-2-phenyl-6-hydroxy-1,2,3,4-tetrahydronaphthalene;

1-(4'-Pyrrolidinoethoxyphonyl)-2-(4"-fluorophenyl)-6-hydroxy-1,2,3,4-tetrahydroisoquinoline;

Cis-6-(4-hydroxyphenyl)-5-[4-(2-piperidin1-yl-ethoxy)-phenyl]-5,6,7,8tetrahydro-naphthalene-2-ol; or 1-(4'-Pyrrolidinolethoxyphenyl)-2-phenyl-6-hydroxy-1,2,3,4-tetrahydroisoquinoline.

6. A pharmaceutical composition according to claim 5 wherein the second compound is PGE$_2$.

7. A pharmaceutical composition according to claim 5 wherein the second compound is 3S(3-Hydroxy-4-phenyl-butyl)-2R-[6-(2H-tetrazol-5-yl)-hexyl-4-]-cyclopentanone.

8. A pharmaceutical composition comprising:
   a. a therapeutically effective amount of a first compound, said first compound being
      Cis-6-(4-fluoro-phenyl)-5-[4-(2-piperidin-1-yl-ethoxy) phenyl]-5,6,7,8-tetrahydro-naphthalene-2-ol;
      (−)-Cis-6-phenyl-5-[4-(2-pyrrolidin-1-yl-ethoxy)-phenyl]-5,6,7,8-tetrahydro-naphthalene-2-ol;
      Cis-6-phenyl-5-[4-(2-pyrrolidin-1-yl-ethoxy)-phenyl]-5,6,7,8-tetrahydro-naphthalene-2-ol;
      Cis-1-[6'-pyrrolodinoethoxy-3'-pyridyl]-2-phenyl-6-hydroxy-1,2,3,4-tetrahydronaphthalene;
      1-(4'-Pyrrolidinoethoxyphenyl)-2-(4"-fluorophenyl)-6-hydroxy-1,2,3,4-tetrahydroisoquinoline;
      Cis-6-(4-hydroxyphenyl)-5-[4-(2-piperidin-1-yl-ethoxy)-phenyl]-5,6,7,8-tetrahydro-naphthalene-2-ol; or
      1-(4'-Pyrrolidinolethoxyphenyl)-2-phenyl-6-hydroxy-1,2,3,4-tetrahydroisoquinoline
   b. a therapeutically effective amount of a second compound, said second compound being sodium fluoride, a parathyroid hormone, or growth hormone.

9. A pharmaceutical composition as recited in claim 8 additionally comprising a pharmaceutical carrier.

10. A pharmaceutical composition as recited in claim 9 wherein the second compound is sodium fluoride.

11. A pharmaceutical a composition as recited in claim 9 wherein the second compound is a parathyroid hormone.

12. A pharmaceutical composition as recited in claim 9 wherein the second compound is growth hormone.

13. A method for treating mammals which present with low bone mass comprising administering to a mammal having a condition which presents with low bone mass the pharmaceutical composition of claim 8.

14. A kit containing a treatment for a condition which presents with low bone mass comprising:
   a. a therapeutically effective amount of
      Cis-6-(4-fluoro-phenyl)-5-[4-(2-piperidin-1-yl-ethoxy) phenyl]-5,6,7,8-tetrahydro-naphthalene-2-ol;
      (−)-Cis-6-phenyl-5-[4-(2-pyrrolidin-1-yl-ethoxy)-phenyl]-5,6,7,8-tetrahydro-naphthalene-2-ol;
      Cis-6-phenyl-5-[4-(2-pyrrolidin-1-yl-ethoxy)-phenyl]-5,6,7,8-tetrahydro-naphthalene-2-ol;
      Cis-1-[6'-pyrrolodinoethoxy-3'-pyridyl]-2-phenyl-6-hydroxy-1,2,3,4-tetrahydronaphthalene;
      1-(4'-Pyrrolidinoethoxyphenyl)-2-(4"-fluorophenyl)-6-hydroxy-1,2,3,4-tetrahydroisoquinoline;
      Cis-6-(4-hydroxyphenyl)-5-[4-(2-piperidin-1-yl-ethoxy)-phenyl]-5,6,7,8-tetrahydro-naphthalene-2-ol; or
      1-(4'-Pyrrolidinolethoxyphenyl)-2-phenyl-6-hydroxy-1,2,3,4-tetrahydroisoquinoline; and a pharmaceutically acceptable carrier in a first unit dosage form;
   b. a therapeutically effective amount of sodium fluoride, a parathyroid hormone, or growth hormone and a pharmaceutically acceptable carrier in a second unit dosage form; and 15. A method for treating a mammal having a condition which presents with low bone mass comprising administering to a mammal having a condition which presents with low bone mass
   a. a therapeutically effective amount of a first compound, said first compound being an estrogen agonist/antagonist; and
   b. a therapeutically effective amount of a second compound, said second compound being a prostaglandin or a prostaglandin agonist/antagonist. wherein the estrogen agonist/antagonist is droloxifene, raloxifene, tamoxifen, 4-hydroxy-tamoxifen, idoxifene, centrachroman,
      Cis-6-(4-fluoro-phenyl)-5-[4-(2-piperidin-1-yl-ethoxy)-phenyl]-5,6,7,8-tetrahydro-naphthalene-2-ol;
      (−)-Cis-6-phenyl-5-[4-(2-pyrrolidin-1-yl-ethoxy)-phenyl]-5,6,7,8-tetrahydro-naphthalene-2-ol;
      Cis-6-phenyl-5-[4-(2-pyrrolidin-1-yl-ethoxy)-phenyl]-5,6,7,8-tetrahydro-aphthalene-2-ol;
      Cis-1-[6'-pyrrolodinoethoxy-3'-pyridyl]-2-phenyl-6-hydroxy-1,2,3,4-tetraydronaphthalene;
      1-(4'-Pyrrolidinoethoxyphenyl)-2-(4"-fluorophenyl)-6-hydroxy-1,2,3,4-tetrahydroisoquinoline;
      Cis-6-(4-hydroxyphenyl)-5-[4-(2-piperidin-1-yl-ethoxy)-phenyl]-5,6,7,8-tetrahydro-naphthalene-2-ol; or
      1-(4'-Pyrrolidinolethoxyphonyl)-2-phenyl-6-hydroxy-1,2,3,4-tetrahydroisoquinoline.

16. A method as recited in claim 15 wherein the estrogen agonist/antagonist is droloxifene, raloxifene, idoxifene, centrachroman,
      Cis-6-(4-fluoro-phenyl)-5-[4-(2-piperidin-1-yl-ethoxy)-phenyl]-5,6,7,8-tetrahydro-naphthalene-2-ol;
      (−)-Cis-6-phenyl-5-[4-(2-pyrrolidin-1-yl-ethoxy)-phenyl]-5,6,7,8-tetrahydro-naphthalene-2-ol;
      Cis-6-phenyl-5-[4-(2-pyrrolidin-1-yl-ethoxy)-phenyl]-5,6,7,8-tetrahydro-naphthalene-2-ol;
      Cis-1-[6'-pyrrolodinoethoxy-3'-pyridyl]-2-phenyl-6-hydroxy-1,2,3,4-tetrahydronaphthalene;
      1-(4'-Pyrrolidinoethoxyphenyl)-2-(4"-fluorophenyl)-6-hydroxy-1,2,3,4-tetrahydroisoquinoline;
      Cis-6-(4-hydroxyphenyl)-5-[4-(2-piperidin-1-yl-ethoxy)-phenyl]-5,6,7,8-tetrahydro-naphthalene-2-ol; or
      1-(4'-Pyrrolidinolethoxyphenyl)-2-phenyl-6-hydroxy-1,2,3,4-tetrahydroisoquinoline.

17. A method as recited in claim 15 wherein the second compound is PGD$_1$, PGD$_2$, PGE$_2$, PGE$_1$, PGF$_2$, PGF$_2\alpha$ or 3S-(3-Hydroxy-4-phenyl-butyl)-2R-[6-(1H-tetrazol-5-yl)-hexyl]-cyclopentanone.

18. A method as recited in claim 17 wherein the estrogen agonist/antagonist is droloxifene.

19. A method as recited in claim 18 wherein the second compound is 3S-(3-Hydroxy-4-phenyl-butyl)-2R-[6-(1H-tetrazol-5-yl)-hexyl]-cyclopentanone.

20. A method as recited in claim 18 wherein the condition which presents with low bone mass is osteoporosis.

21. A method as recited in claim 18 wherein the first compound and the second compounds are administered substantially simultaneously.

22. A method as recited in claim 18 wherein the second compound is administered for a period of from about three months to about three years.

23. A method as recited in claim 22 followed by administration of the first compound for a period of from about three months to about three years without the administration of the second compound during the period of from about three months to about three years.

24. A method as recited in claim 22 followed by administration of the first compound for a period greater than about three years without the administration of the second compound during the greater than about three year period.

25. A method as recited in claim 17 wherein the estrogen agonist/antagonist is

Cis-6-(4-fluoro-phenyl)-5-[4-(2-piperidin-1-yl-ethoxy)-phenyl]-5,6,7,8- tetrahydro-naphthalene-2-ol; (-)-Cis-6-phenyl-5-[4-(2-pyrrolidin-1-yl-ethoxy)-phenyl]-5,6,7,8- tetrahydro-naphthalene-2-ol;

Cis-6-phenyl-5-[4-(2-pyrrolidin-1-yl-ethoxy)-phenyl]-5,6,7,8,- tetrahydro-naphthalene-2-ol;

Cis-1-[6'-pyrrolodinoethoxy-3'-pyrridyl]-2-phenyl6-hydroxy-1,2,3,4- tetrahydronaphthalene;

1-(4'-Pyrrolidinoethoxyphenyl)-2(4"-fluorophenyl)-6-hydroxy-1,2,3,4- tetrahydroisoquinoline;

Cis-6-(4-hydroxyphenyl)-5[4 -(2-piperidin-1-yl-ethoxy)-phenyl]-5,6,7,8- tetrahydro-naphthalene-2-ol; or 1-(4'-Pyrrolidinolethoxyphenyl)-2-phenyl-6-hydroxy-1,2,3,4- tetrahydroisoquinoline.

26. A method as recited in claim 25 wherein the second compound is $PGE_2$.

27. A method as recited in claim 25 wherein the second compound is 3S-(3-Hydroxy-4-phenyl-butyl)-2R-[6-(1H-tetrazol-5yl)-hexyl]-cyclopentanone.

28. A method as recited in claim 25 wherein the condition which presents with low bone mass is osteoporosis.

29. A method as recited in claim 25 wherein the first compound and the second compounds are administered substantially simultaneously.

30. A method as recited in claim 25 wherein the second compound is administered for a period of from about three months to about three years.

31. A method as recited in claim 30 followed by administration of the first compound for a period of from about three months to about three years without the administration of the second compound during the period of from about three months to about three years.

32. A method as recited in claim 30 followed by administration of the first compound for a period greater than about three years without the administration of the second compound during the greater than about three year period.

33. A method for treating a mammal having a condition which presents with low bone mass comprising administering to a mammal having a condition which presents with low bone mass a. a therapeutically effective amount of a first compound, said first compound being Cis-6-(4-fluoro-phenyl)-5-[4-(2-piperidin-1-yl-ethoxy)phenyl]-5,6,7,8-tetrahydro-naphthalene-2-ol;

(-)-Cis-6-phenyl-5-[4-(2-pyrrolidin-1-yl-ethoxy)-phenyl]-5,6,7,8-tetrahydro-naphthalene-2-ol;

Cis-6-phenyl-5-[4-(2-pyrrolidin-1-yl-ethoxy)-phenyl]-5,6,7,8-tetrahydro-naphthalene-2-ol;

Cis-1-[6'-pyrrolodinoethoxy-3'-pyridyl]-2-phenyl-6-hydroxy-1,2,3,4-tetrahydronaphthalene;

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydro-naphthalene-2-ol; or 1-(4'-Pyrrolidinolethoxyphenyl)-2-phenyl-6-hydroxy-1,2,3,4-tetrahydroisoquinoline; and b. a therapeutically effective amount of a second compound, said second compound being sodium fluoride, a parathyroid hormone, or growth hormone.

34. A method as recited in claim 33 wherein the second compound is sodium fluoride.

35. A method as recited in claim 33 wherein the second compound is a parathyroid hormone.

36. A method as recited in claim 33 wherein the second compound is growth hormone.

37. A method as recited in claim 33 wherein the condition which presents with low bone mass is osteoporosis.

38. A method as recited in claim 33 wherein the first compound and the second compound are administered substantially simultaneously.

39. A method as recited in claim 33 wherein the second compound is administered for a period of from about three months to about three years.

40. A method as recited in claim 39 followed by administration of the first compound for a period of from about three months to about three years without the administration of the second compound during the period of from about three months to about three years.

41. A method as recited in claim 39 followed by administration of the first compound for a period greater than about three years without the administration of the second compound during the greater than about three year period.

* * * * *